United States Patent
Tanabe

(10) Patent No.: US 9,068,944 B2
(45) Date of Patent: *Jun. 30, 2015

(54) OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

(71) Applicant: OLYMPUS CORPORATION, Tokyo (JP)

(72) Inventor: Tetsuya Tanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 56 days.

This patent is subject to a terminal disclaimer.

(21) Appl. No.: 14/036,921

(22) Filed: Sep. 25, 2013

(65) Prior Publication Data

US 2014/0024020 A1    Jan. 23, 2014

Related U.S. Application Data

(63) Continuation of application No. PCT/JP2012/058840, filed on Apr. 2, 2012.

(30) Foreign Application Priority Data

Apr. 13, 2011   (JP) .................. 2011-089646

(51) Int. Cl.
*G01N 21/64* (2006.01)
*G01N 15/14* (2006.01)
(Continued)

(52) U.S. Cl.
CPC ............ *G01N 21/64* (2013.01); *G01N 21/6408* (2013.01); *G01N 21/6452* (2013.01);
(Continued)

(58) Field of Classification Search
USPC .............. 356/335–339, 317, 318; 250/203.3, 250/459.1, 458.1, 216, 205
See application file for complete search history.

(56) References Cited

U.S. PATENT DOCUMENTS 4,251,733 A    2/1981  Hirleman, Jr.
4,580,895 A *  4/1986  Patel ............................ 356/39
(Continued)

FOREIGN PATENT DOCUMENTS

EP    1630546 A1    3/2006
EP    1 906 172 A1  4/2008
(Continued)

OTHER PUBLICATIONS

Extended European Search Report dated Oct. 20, 2014, issued in corresponding European Patent Application No. 12770835.2 (10 pages).

(Continued)

*Primary Examiner* — Sang Nguyen
(74) *Attorney, Agent, or Firm* — Westerman, Hattori, Daniels & Adrian, LLP

(57) ABSTRACT

There is provided a structure to reduce the size of light intensity data in the scanning molecule counting method using an optical measurement with a confocal microscope or a multiphoton microscope. In the inventive optical analysis technique of detecting light of a light-emitting particle in a sample solution, time series light intensity data of light from a light detection region detected with moving the position of the light detection region of the microscope in the sample solution is generated, and a signal of a light-emitting particle individually is detected in the time series light intensity data. In that case, regions where no signal indicating light of light-emitting particles exist in the time series light intensity data is removed from the time series light intensity data.

33 Claims, 9 Drawing Sheets

(51) Int. Cl.
*G02B 21/00* (2006.01)
*G02B 21/16* (2006.01)
*G02B 21/36* (2006.01)
*G01N 21/51* (2006.01)
*G01N 21/76* (2006.01)

(52) U.S. Cl.
CPC ............ *G01N21/6458* (2013.01); *G01N 15/14* (2013.01); *G01N 21/51* (2013.01); *G02B 21/0076* (2013.01); *G02B 21/16* (2013.01); *G01N 21/76* (2013.01); *G01N 21/763* (2013.01); *G02B 21/367* (2013.01); *G01N 15/1429* (2013.01); *G01N 15/1434* (2013.01)

(56) References Cited

U.S. PATENT DOCUMENTS

| | | | |
|---|---|---|---|
| 5,866,336 | A | 2/1999 | Nazarenko et al. |
| 6,280,960 | B1 | 8/2001 | Carr |
| 6,320,196 | B1 * | 11/2001 | Dorsel et al. ............... 250/458.1 |
| 6,376,843 | B1 | 4/2002 | Palo |
| 6,388,746 | B1 | 5/2002 | Eriksson et al. |
| 6,388,788 | B1 | 5/2002 | Harris et al. |
| 6,400,487 | B1 | 6/2002 | Harris et al. |
| 6,403,338 | B1 | 6/2002 | Knapp et al. |
| 6,710,871 | B1 | 3/2004 | Goix |
| 6,856,391 | B2 | 2/2005 | Garab et al. |
| 6,927,401 | B1 | 8/2005 | Palo |
| 7,534,987 | B2 * | 5/2009 | Mitani ........................ 250/216 |
| 8,284,484 | B2 | 10/2012 | Hoult et al. |
| 2001/0035954 | A1 | 11/2001 | Rahn et al. |
| 2002/0008211 | A1 | 1/2002 | Kask |
| 2002/0036775 | A1 | 3/2002 | Wolleschensky et al. |
| 2002/0051805 | A1 * | 5/2002 | Ueki et al. .................... 424/422 |
| 2002/0109100 | A1 * | 8/2002 | Jackson et al. ............. 250/458.1 |
| 2003/0036855 | A1 | 2/2003 | Harris et al. |
| 2003/0218746 | A1 | 11/2003 | Sampas |
| 2004/0022684 | A1 | 2/2004 | Heinze et al. |
| 2004/0051051 | A1 | 3/2004 | Kato et al. |
| 2004/0150880 | A1 | 8/2004 | Nakata et al. |
| 2005/0260660 | A1 | 11/2005 | van Dongen et al. |
| 2006/0078998 | A1 | 4/2006 | Puskas et al. |
| 2006/0109461 | A1 * | 5/2006 | Ishibashi ....................... 356/318 |
| 2006/0158721 | A1 | 7/2006 | Nakata et al. |
| 2006/0256338 | A1 | 11/2006 | Gratton et al. |
| 2007/0024964 | A1 * | 2/2007 | Ishibashi et al. .............. 359/380 |
| 2008/0052009 | A1 | 2/2008 | Chiu et al. |
| 2008/0117421 | A1 * | 5/2008 | Yamaguchi et al. .......... 356/417 |
| 2009/0159812 | A1 | 6/2009 | Livingston |
| 2009/0290780 | A1 | 11/2009 | Kottig |
| 2010/0033718 | A1 | 2/2010 | Tanaami |
| 2010/0177190 | A1 | 7/2010 | Chiang et al. |
| 2010/0202043 | A1 | 8/2010 | Ujike |
| 2010/0251438 | A1 | 9/2010 | Huber et al. |
| 2010/0301231 | A1 * | 12/2010 | Yamaguchi ................. 250/459.1 |
| 2012/0318956 | A1 * | 12/2012 | Yamaguchi et al. ....... 250/203.3 |

FOREIGN PATENT DOCUMENTS

| | | | |
|---|---|---|---|
| EP | 2602613 | A1 | 6/2013 |
| JP | 04-337446 | A | 11/1992 |
| JP | 10-512952 | A | 12/1998 |
| JP | 2002-507762 | A | 3/2002 |
| JP | 2002-543414 | A | 12/2002 |
| JP | 2004-506192 | A | 2/2004 |
| JP | 2005-98876 | A | 4/2005 |
| JP | 2005-099662 | A | 4/2005 |
| JP | 2007-020565 | A | 2/2007 |
| JP | 4023523 | B2 | 12/2007 |
| JP | 2008-116440 | A | 5/2008 |
| JP | 2008-536093 | A | 9/2008 |
| JP | 2008-292371 | A | 12/2008 |
| JP | 2009-145242 | A | 7/2009 |
| JP | 2009-281831 | A | 12/2009 |
| JP | 2009-288161 | A | 12/2009 |
| JP | 2010-017127 | A | 1/2010 |
| JP | 2010-190730 | A | 9/2010 |
| JP | 2011-02415 | A | 1/2011 |
| JP | 2011-508219 | A | 3/2011 |
| WO | 98/16814 | A1 | 4/1998 |
| WO | 99/47963 | A1 | 9/1999 |
| WO | 00/66985 | A1 | 11/2000 |
| WO | 02/12864 | A1 | 2/2002 |
| WO | 2006/084283 | A2 | 8/2006 |
| WO | 2007/010803 | A1 | 1/2007 |
| WO | 2007/118209 | A2 | 10/2007 |
| WO | 2007/147159 | A2 | 12/2007 |
| WO | 2008/007580 | A1 | 1/2008 |
| WO | 2008/080417 | A1 | 7/2008 |
| WO | 2009/117033 | A2 | 9/2009 |
| WO | 2011/108369 | A1 | 9/2011 |
| WO | 2011/108370 | A1 | 9/2011 |
| WO | 2011/108371 | A1 | 9/2011 |
| WO | 2012/014778 | A1 | 2/2012 |
| WO | 2012/032955 | A1 | 3/2012 |
| WO | 2012/032981 | A1 | 3/2012 |
| WO | 2012/039352 | A1 | 3/2012 |

OTHER PUBLICATIONS

Kinjo, Masataka, "Single molecule protein, nucleic acid, and enzyme assays and their procedures; Single molecule detection by fluorescence correlation spectroscopy", Protein, Nucleic Acid, Enzyme, 1999, vol. 44, No. 9, pp. 1431-1438, w/ English translation.

Almes-Meyer, F.J., "Nanoparticle Immunoassays: A new Method for Use in Molecular Diagnostics and High Throughput Pharmaceutical Screening based on Fluorescence Correlation Spectroscopy", edit. R. Rigler, Springer, Berlin, 2000, pp. 204-224.

Kato, Noriko et al., "A single molecule analyzer that enable new analysis of DNA and protein interactions", Gene Medicine, 2002, vol. 6, No. 2, pp. 271-277.

Peet Kask et al., "Fluorescence-intensity distribution analysis and its application in biomolecular detection technology", PNAS, vol. 96, No. 24, Nov. 23, 1999, pp. 13756-13761.

International Search Report dated Jun. 26, 2012, issued in corresponding application No. PCT/JP2012/058840.

Park, Mira et al., "Counting the Number of Fluorophores Labeled in Biomolecules by Observing the Fluorescence-Intensity Transient of a Single Molecule" Bulletin of the Chemical Society of Japan, dated Aug. 30, 2005, vol. 78, No. 9, p. 1612-1618.

U.S. Office Action dated Apr. 2, 2013, issued in related U.S. Appl. No. 13/596,280.

Kask, Peet et al., "Two-Dimensional Fluorescence Intensity Distribution Analysis: Theory and Applications", Biophysical Journal, Apr. 2000, vol. 78, p. 1703-1713.

Chinese Office Action dated Aug. 13, 2013, issued in related Chinese application No. 2011800116553; w/ English Translation (16 pages).

International Search Report dated Mar. 29, 2011, issued in related PCT/JP2011/053483.

International Preliminary Report on Patentability (PCT/IPEA/409) issued in related PCT/JP2011/053483, Dated 2011.

Chinese Office Action dated Aug. 9, 2013, issued in related Chinese application No. 201180011640.7; w/ English Translation (16 pages).

International Search Report dated Mar. 29, 2011, issued in related PCT/JP2011/053482.

International Preliminary Report on Patentability (PCT/IPEA/409) issued in related PCT/JP2011/053482, Dated 2011.

U.S. Office Action dated Jan. 3, 2013, issued in related U.S. Appl. No. 13/597,825.

Chinese Office Action dated Feb. 7, 2013, issued in related Chinese application No. 201180011644.5; w/ English Translation (18 pages).

Extended European Search Report dated Mar. 28, 2013, issued in related EP application No. 11750481.1.

International Search Report dated Mar. 29, 2011, issued in related PCT/JP2011/053481.

International Preliminary Report on Patentability (PCT/IPEA/409) issued in related PCT/JP2011/053481, Dated 2011.

Goodwin, Peter et al., "Rapid Sizing of Individual Fluorescently Stained DNA Fragments by Flow Cytometry," Nucleic Acids Research, 1993, vol. 21, No. 4, p. 803-806.

(56) References Cited

OTHER PUBLICATIONS

Keller, Richard et al., "Single-Molecule Fluorescence Analysis in Solution," Applied Spectroscopy, 1996, vol. 50, No. 7, p. 12A-32A.
Lee, Yuan-Hsiang et al., "Laser-Induced Fluorescence Detection of a Single Molecule in a Capillary," Analytical Chemistry, dated Dec. 1, 1994, vol. 66, No. 23, p. 4142-4149.
Li, Haitao et al., "Ultrasensitive Coincidence Fluorescence Detection of Single DNA Molecules," Analytical Chemistry, dated Apr. 1, 2003, vol. 75, No. 7, p. 1664-1670.
Nie, Shuming et al., "Probing Individual Molecules with Confocal Fluorescence Microscopy," Science, dated Nov. 11, 1994, vol. 266, p. 1018-1021.
Tahari, Abdel. "Fluorescence Correlation Spectroscopy: Ultrasensitive Detection in Clear and Turbid Media," University of Illinois, 2006, p. 1-88.
Wu, Alan et al., "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, p. 2157-2159.
Itoh et al., "A New Method for Detection of Influenza Viruses by Single Particle-Recognition Based on the Principle of Fluorescence Correlation Spectroscopy," Chemistry and Biology, 2009, vol. 47, No. 12, p. 823-830.
Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.
U.S. Office Action dated Oct. 4, 2013, issued in related U.S. Appl. No. 13/596,243.
Japanese Office Action dated Dec. 18, 2012 issued in related JP application No. 2012-503060; w/ English Translation (6 pages).
International Search Report dated Nov. 29, 2011, issued in related PCT/JP2011/071196.
Guo, Xiang-Qun et al., "Use of a Long-Lifetime Re(I) Complex in Fluorescence Polarization Immunoassays of High-Molecular-Weight Analytes", Analytical Chemistry, Feb. 1998, vol. 7, No. 3, p. 632-637.
International Search Report dated Jun. 26, 2012, issued in related PCT/JP2012/057731.
International Search Report dated Aug. 14, 2012, issued in related PCT/JP2012/066943.
International Search Report dated Mar. 5, 2013, issued in related PCT/JP2013/052446.
Supplementary European Search Report dated Feb. 13, 2014, issued in related EP application No. 11826797.0.
International Search Report dated Nov. 29, 2011, issued in related PCT/JP2011/072939.

\* cited by examiner

FIG. 1A
FIG. 1B
FIG. 1C
FIG. 1D
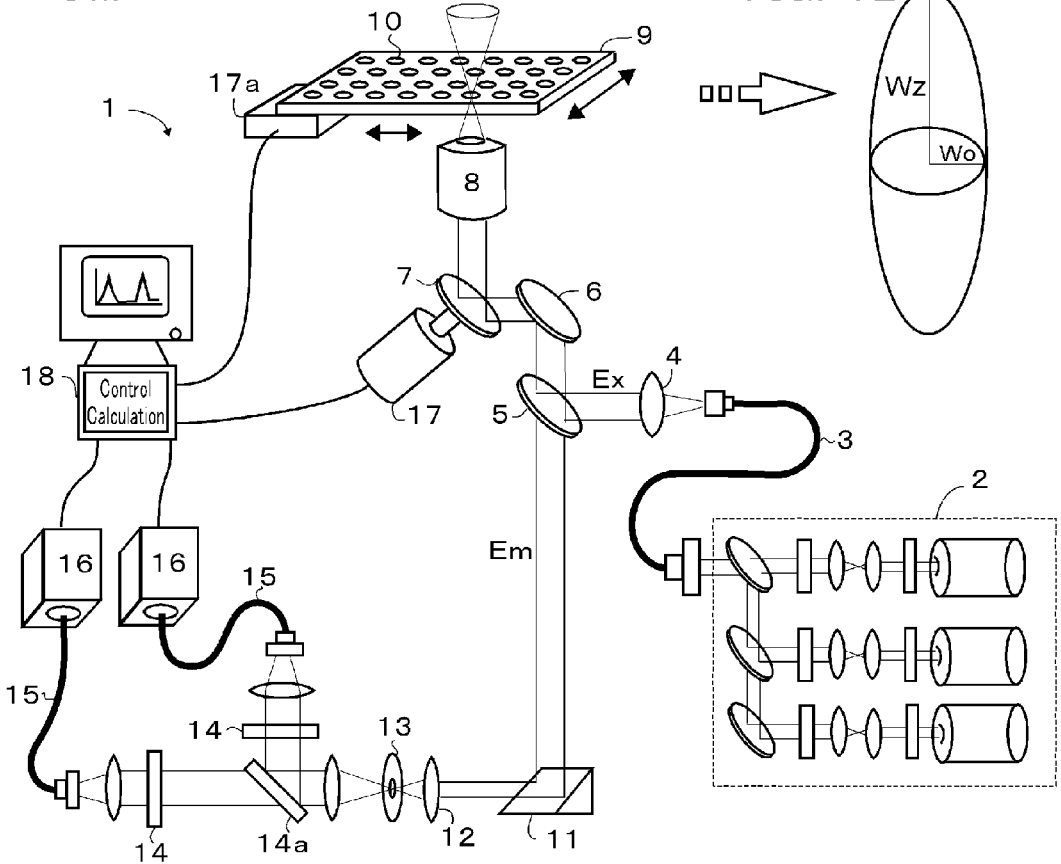
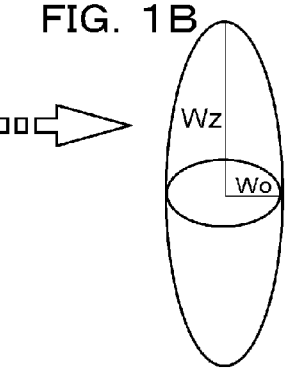
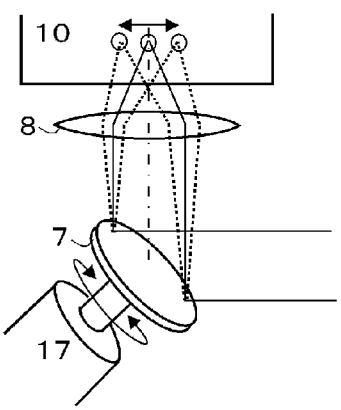
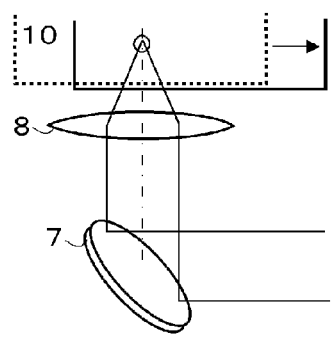

High Concentration (e. g. ~ 1nM)

Low Concentration (e. g. ~ 1pM)

OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

TECHNICAL FIELD

This invention relates to an optical analysis technique capable of detecting light from a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to an optical analysis device, optical analysis method and computer program for optical analysis, which detect individually the light from a single particle which emits light, using an optical system as described above, to make it possible to conduct various optical analyses. In this regard, in this specification, a particle which emits light (hereafter, referred to as a "light-emitting particle") may be any of a particle which itself emits light and a particle to which an arbitrary light-emitting label or light-emitting probe has been attached, and the light emitted from a light-emitting particle may be fluorescence, phosphorescence, chemiluminescence, bioluminescence, scattered light, etc.

BACKGROUND ART

According to the developments in optical measurement techniques in recent years, detection and/or measurement of faint light at the single photon or single fluorescent molecule level have become possible by using an optical system of as confocal microscope and a super high sensitive light detection technique capable of the photon counting (single photon detection). Thus, there are variously proposed devices or methods of performing detection of a characteristic, an intermolecular interaction, a binding or dissociating reaction of a biological molecule, etc. by means of such a faint light measurement technique. For example, in Fluorescence Correlation Spectroscopy (FCS, see e.g. patent documents 1-3 and non-patent documents 1-3), by means of the optical system of a laser confocal microscope and a photon counting technique, there is performed the measurement of fluorescence intensity of fluorescent molecules or fluorescently labeled molecules (fluorescent molecules, etc.), entering into and exiting out of a micro region (the focal region to which the laser light of the microscope is condensed, called a "confocal volume") in a sample solution, and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 4, non-patent document 4) or Photon Counting Histogram (PCH, e.g. patent document 5), there is generated a histogram of fluorescence intensity of fluorescent molecules, etc., entering into and exiting out of a confocal volume, measured similarly to FCS; and the average value of the characteristic brightness of the fluorescent molecules, etc. and the average number of molecules dwelling in the confocal volume are calculated by fitting a statistical model formula to the distribution of the histogram, so that, based on the information thereof, the structure or size changes, binding or dissociative conditions or dispersion and aggregation conditions of molecules can be estimated. In addition, in patent documents 6 and 7, there are proposed methods of detecting fluorescent substances based on a time progress of fluorescence signals of a sample solution measured using the optical system of a confocal microscope. Patent document 8 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the methods employing the measurement technique of fluorescent light of a micro region using the optical system of a confocal microscope and a photon counting technique, such as FCS and FIDA, a sample amount required for the measurement may be extremely small (an amount used in one measurement is at most several tens of μL), and its concentration is extremely low as compared with the prior art, and the measuring time is also shortened extremely (In one measurement, a measuring process for time of order of seconds is repeated several times.). Thus, those techniques are expected to be a strong tool enabling an experiment or a test at low cost and/or quickly in comparison with conventional biochemical methods, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523.
Patent document 5 WO 2008-080417
Patent document 6: Japanese Patent laid-open publication No. 2007-20565
Patent document 7: Japanese Patent laid-open publication No. 2008-116444
Patent document 8: Japanese Patent laid-open publication No. 4-337446

Non-Patent Documents

Non-patent document 1: Masataka Kaneshiro; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.

Non-patent document 3: Noriko Kato, et al. "Gene medicine", Vol. 6, No. 2, pages 271-277.

Non-patent document 4: P. Kask, K. Palo, D. Ullmann, K. Gall PNAS 96, 13756-13701 (1999)

SUMMARY OF INVENTION

Technical Problem

In the above-mentioned optical analysis technique using the optical system of a confocal microscope and a photon counting technique, such as FCS, and FIDA, although the measured light is the light emitted from single or several fluorescent molecules, there are conducted in the analysis of the light the statistical procedures for the calculating of the fluorescence intensity fluctuation, etc., such as the computation of the autocorrelation function or the fitting to the histogram of fluorescence intensity data measured in time series, and therefore the signal of the light from an individual fluorescent molecule is not seen or analyzed. That is, in these optical analysis techniques, through the statistical processing of the signals of the lights from a plurality of fluorescent molecules, etc., statistical average characteristics of the fluorescent molecules, etc, will be detected. Thus, in order to obtain a statistically significant result in these optical analysis techniques, the concentration or number density of a fluorescent molecule, etc. to be an observation object in the sample solution should be at such a level that fluorescent molecules, etc. of the number enabling a statistical process will enter in and exit from a micro region in one measuring term of a length of order of seconds in an equilibrium, preferably at such a level that about one fluorescent molecule, etc. will be always present in the micro region. Actually, since the volume of a confocal volume is about 1 fL, the concentration of a fluorescent molecule, etc. in a sample solution used in the above-mentioned optical analysis technique is typically at the level of 1 nM or more, and at much less than 1 nM, there is produced a term in which no fluorescent molecules, etc. are present in the confocal volume, so that no statistically significant analysis result will be obtained. On the other hand, in the detection methods of fluorescent molecules, etc. described in patent documents 6-8, no statistical computation processes of fluorescence intensity fluctuation are included so that fluorescent molecules, etc. even at less than 1 nM in a sample solution can be detected, but, it has not been achieved to compute quantitatively the concentration or number density of a fluorescent molecule, etc. moving at random in a solution.

Then, in Japanese patent application No. 2010-044714 and PCT/JP2011/63481, Applicant of the present application has proposed an optical analysis technique based on a new principle which makes it possible to observe quantitatively a condition or characteristic of a light-emitting particle in a sample solution where the concentration or number density of the light-emitting particle to be an observation object is lower than the level at Which the optical analysis techniques including statistical procedures, such as FCS and FIDA, etc. are used. In this new optical analysis technique, briefly, there is used an optical system which can detect light from a micro region in a solution, such as an optical system of a confocal microscope or a multiphoton microscope, similarly to FCS, FIDA, etc., and additionally, the position of the micro region, i.e. the detection region of light (called "light detection region" in the following) is moved in the sample solution, namely, the inside of the sample solution is scanned with the light detection region, and when the light detection region encompasses a light-emitting particle, dispersed and moving at random in the sample solution, the light emitted from the light-emitting particle is detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter.), not only a sample amount necessary for measurement may be small (for example, about several 10 µL) and the measuring time is short similarly to optical analysis techniques, such as FCS and FIDA, but also, it becomes possible to detect the presence of a light-emitting particle and to quantitatively detect its characteristic, such as a concentration, a number density, etc., at a lower concentration or number density, as compared with the case of optical analysis techniques, such as FCS and FIDA.

In the above-mentioned scanning molecule counting method, more concretely, light intensity values (or photon count values) sequentially measured with moving the position of a light detection region in a sample solution are recorded as time series light intensity data, and on the data, a region having a change of the intensity indicating the light emitted from a light-emitting particle is detected. Namely, the region where significant information exists on time series light intensity data is a region with the intensity change indicating the light from a light-emitting particle, and the other regions are unnecessary regions. Thus, the recording and storing of regions where no significant information exists, i.e., regions without intensity change indicating the light from a light-emitting particle may vainly increase the size of time series light intensity data and vainly use memory volumes of a storage device. And, since regions without intensity change indicating the light from a light-emitting particle on time series light intensity data increases as the light-emitting particle concentration in a sample solution is lower, vainly used memory volumes will increase. Further, the increase of the data volume of time series light intensity data causes the increase of data processing load and time in the computer.

Thus, one of objects of the present invention is propose a new way of making it possible to reduce the data volume of time series light intensity data in the scanning molecule counting method as described above.

Further, another object of the present invention is to make it possible to save memory volumes for storing data and reduce the load and time of data processing by the reduction of the data volume of time series light intensity data processed in the scanning molecule counting method as described above.

Solution to Problem

According to one aspect of the present invention, the above-mentioned object is achieved by an optical analysis device which detects light from a light-emitting particle dispersed and moving at random in a sample solution using an optical system of a confocal microscope or a multiphoton microscope, characterized by comprising: a light detection region mover which moves a position of a light detection region of the optical system of the microscope in the sample solution; a light detector which detects light from the light detection region; and a signal processor which generates time series light intensity data of the light from the light detection region detected with the light detector with moving the position of the light detection region in the sample solution and detects a signal indicating light from each light-emitting particle individually in the time series light intensity data;

wherein the signal processor removes from the time series light intensity data regions where no signal indicating light from each light-emitting particle in time series light intensity data exists. In this structure, "a light-emitting particle dispersed and moving at random in a sample solution" may be a particle, such as an atom, a molecule or an aggregate of these, which is dispersed or dissolved in a sample solution and emits light, and it may be an arbitrary particulate matter making the Brownian motion freely in a solution without being fixed on a substrate, etc. The light-emitting particle is typically a fluorescent particle, but may be a particle which emits light by phosphorescence, chemiluminescence, bioluminescence, light scattering, etc. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the spatial relationship of an objective and a pinhole. For a light-emitting particle which emits light without illumination light, for example, a molecule which emits light according to chemiluminescence or bioluminescence, no illumination light is required in the microscope.). Further, in the followings in this specification, "a signal of a light-emitting particle" means "a signal expressing light from a light-emitting particle" unless noted otherwise.

As understood from the above, in the basic structure of the present invention, i.e., the scanning molecule counting method, the light detection is sequentially performed while the position of a light detection region is moved in a sample solution, namely, while the inside of the sample solution is scanned with the light detection region. Then, when the light detection region moving in the sample solution encompasses a randomly moving light-emitting particle, the light from the light-emitting particle is detected by the light detector, and thereby, it is expected that the existence of one particle will be detected. Thus, in the sequentially detected light, a signal indicating the light from a light-emitting particle is individually detected, and thereby, the individual existences of light-emitting particles are detected one by one, and accordingly, diverse information on the condition of a particle in the solution will be acquired. In that case, as already noted, the regions having no intensity change indicating light from a light-emitting particle in the group of the light intensity values measured sequentially, i.e., time series light intensity data, are unnecessary regions, so that those vainly increase the size of the time series light intensity data and vainly use the memory volumes of a storage device, and also, the load and processing time of data processing in the signal process of detecting a signal indicating light from a light-emitting particle from the time series light intensity data may increase. Thus, in the present invention, as above, the signal processor is designed to perform an operation of removing from the time series light intensity data regions where no signal indicating light from each light-emitting particle in the time series light intensity data exists.

In the structure of the above-mentioned present invention, in general, it is possible to distinguish between a region where a signal indicating light from each light-emitting particle exists and a region where no signal indicating light from each light-emitting particle exists in time series light intensity data based on characteristics of the light intensity data in those regions. Namely, on time series light intensity data, the value of the output of the light detector changes in pulse form in the time section where light from a light-emitting particle has arrived at the light detector, which time section has a characteristic different from that of the time section where only a noise has been generated while no light from light-emitting particles has come, and therefore, by referring to such a characteristic showing the presence or absence of the light from a light-emitting particle, it will become possible to identify a region where no signal indicating light from each light-emitting particle exists in time series light intensity data. Thus, in the inventive device, the signal processor may be designed to compute out a characteristic value of the light intensity which shows the presence or absence of the light from a light-emitting particle in every time section of a predetermined width in the time series light intensity data, determine time sections where no signal indicating light from each light-emitting particle exists using the characteristic value, and remove from time series light intensity data the regions corresponding to the time section where no signal indicating light from each light-emitting particle exists.

As a characteristic value of the light intensity showing the presence or absence of light from a light-emitting particle as described above, an arbitrary value whose magnitude in a time section of a predetermined width where light from a light-emitting particle exists becomes larger than the magnitude in a time section of the predetermined width where no light from a light-emitting particle exists is employable. In that case, when the characteristic value of the light intensity is larger than a predetermined threshold value, it is judged that a signal from a light-emitting particle exists in the time section of the predetermined width. Such a characteristic value may be, for example, either of the integrated value of light intensities, the center value of light intensities, the average of light intensities, the standard deviation of light intensities, the variance of light intensities, the entropy of light intensities, the maximum of light intensities and the particle count computed from the value of the autocorrelation function of light intensities when the correlation time is set to 0 in a time section of a predetermined width. In this regard, typically, the light detector detects the light from the light detection region by photon counting, and in this case, the time series light intensity data is time series photon count data. Accordingly, the characteristic value of light intensity may be a value selected from a group of the total sum of photon counts, the center value of photon counts, the average of photon counts, the standard deviation of photon counts, the variance of photon counts, the entropy of photon counts, the maximum of photon counts and the particle count computed from the value of the autocorrelation function of photon counts when the correlation time is set to 0 in a time section of a predetermined width.

Further, in the above-mentioned inventive device, the removal from the time series light intensity data regions where no signal indicating light from each light-emitting particle the in time series light intensity data exists may be conducted in before or after the individual detection processing of a signal indicating light from each light-emitting particle in the time series light intensity data. In a case of removing regions where no signal of a light-emitting particle exists before the individual detection processing of a signal of a light-emitting particle, it is advantageous in that the load and processing time of data processing of the device for the individual detection processing of a signal of a light-emitting particle are reduced. Accordingly, in the inventive device, the signal processor may be designed to detect individually a signal indicating light from each light-emitting particle on the time series light intensity data from which regions where no signal indicating light from each light-emitting particle in time series light intensity data exists have been removed. In this regard, in a case of removing regions where no signals of light-emitting particles exist after the individual detection processing of a signal of a light-emitting particle, it is advantageous in that the accuracy of the individual detection processing of a signal of a light-emitting particle is ensured. Even in either of the cases, in order to save the memory volume of a storage device, the signal processor may be designed to store in the storage device light intensity data obtained by removing from the time series light intensity data regions where no signal indicating light from each light-emitting particle exists.

Furthermore, in the process of the signal processor of the inventive device, the individual detection of a signal indicating light from each light-emitting particle may be performed based on the shape of the time series signal. In one embodiment, typically, it may be detected that one light-emitting particle entered into the light detection region when a signal having a larger intensity than a predetermined threshold value is detected.

In the above-mentioned inventive device, the moving speed of the position of the light detection region in the sample solution may be appropriately changed based on the characteristic or the number density or concentration of the light-emitting particle in the sample solution. As understood in a person skilled in the art, the condition of detected light from the light-emitting particle may change in accordance with its characteristic, number density or concentration in the sample solution. Especially, when the moving speed of the light detection region becomes quick, the amount of light obtained from one light-emitting particle will be reduced, and therefore it is preferable that the moving speed of the light detection region can be changed appropriately so that the light from one light-emitting particle can be measured precisely or with sufficient sensitivity.

Furthermore, the moving speed of the position of the light detection region in the sample solution is preferably set to be higher than the diffusional moving velocity of a light-emitting particle (the average moving speed of a particle owing to the Brownian motion). As explained above, in the inventive device, a light-emitting particle will be detected individually by detecting the light emitted from the light-emitting particle in the light detection region when the light detection region passes through the existence position of the light-emitting particle. However, when the light-emitting particle moves at random owing to the Brownian motion to move into and out of the light detection region multiple times, it is possible that the signal from one light-emitting particle (showing its existence) will be detected multiple times, and therefore it would become difficult to make the existence of one light-emitting particle associated with the detected signal. Then, as described above, the moving speed of the light detection region is set higher than the diffusional moving velocity of a light-emitting particle, and thereby it becomes possible to make one light-emitting particle correspond to one signal. In this regard, since the diffusional moving velocities differ depending upon light-emitting particles, it is preferable that the moving speed of the light detection region can be changed appropriately according to the characteristics (especially, the diffusion constant) of the light-emitting particle as described above.

The moving of the position of the light detection region may be done in an arbitrary way. For example, the position of the light detection region may be changed by changing the optical path using a galvanomirror employed in the laser scan type optical microscope, or the position of the light detection region within the sample solution may be moved by fixing the light detection region and moving the position of the sample solution (e.g. by moving the stage of the microscope). The movement track of the position of the light detection region may be set arbitrarily, for example, which is selectable from circular, elliptical, rectangular, straight, and curvilinear ones. Especially, in the case that the position of the light detection region is moved by changing the optical path of the optical system, the movement of the light detection region is quick without substantial generation of mechanical vibration and hydrodynamic effect in the sample solution, and therefore, the measurement of light can be performed advantageously under a stable condition without dynamic action affecting the light-emitting particle to be detected in the sample solution.

In one of manners of the above-mentioned present invention, the number of light-emitting particles encompassed in the light detection region may be counted by counting the number of signals (The counting of particles). In that case, by associating the number of the detected light-emitting particles with the moving amount of the position of the light detection region, the information on the number density or concentration of the light-emitting particle identified in the sample solution will be acquired. Concretely, for instance, the ratio of number densities or concentrations of two or more sample solutions or a relative ratio of a number density or concentration to that of a standard sample solution to be the reference for a concentration or a number density may be computed, or an absolute number density value or concentration value may be determined using a relative ratio of a number density or concentration to that of a standard sample solution to be the reference for a concentration or a number density. Or, by determining the whole volume of the moving track of the position of the light detection region by an arbitrary method, for example, by moving the position of the light detection region at a predetermined speed, the number density or concentration of the light-emitting particle can be concretely computed.

The processes of the optical analysis technique of conducting a light detection with moving the position of a light detection region in a sample solution and detecting the signal from each light-emitting particle individually in the above-mentioned inventive device, in which the reduction of the size of light intensity data is possible, can be realized with a general-purpose computer. Thus, according to another aspect of the present invention, there is provided a computer readable storage device having a computer program product including programmed instructions for optical analysis for detecting light from a light-emitting particle dispersed and moving at random in a sample solution using an optical system of a confocal microscope or a multiphoton microscope, said programmed instructions causing a computer to perform steps of: moving a position of a light detection region of the optical system of the microscope in the sample solution; detecting light from the light detection region during moving the position of the light detection region in the sample solution and generating time series light intensity data, and detecting individually a signal indicating light from each light-emitting particle in the time series light intensity data, the computer program, further including a procedure of removing regions where no signal indicating light from each light-emitting particle in time series light intensity data exists from the time series light intensity data. In the present application, "computer readable storage device" does not cover transitory propagating signal per se. A computer reads out the program memorized in the storage device and realizes the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program. In this structure, typically, in the step of detecting the light from the light detection region and generating the time series light intensity data, the light from the light detection region is detected by photon counting, and in that case, the time series light intensity data is time series photon count data. Also, in the above-mentioned computer readable storage device, in the step of detecting individually a signal indicating light from each light-emitting particle in the time series light intensity data, the signal indicating light from each light-emitting particle may be individually detected on a light intensity data obtained by removing the regions where no signal indicating light from each light-emitting particle in time series light intensity data exists from time series light intensity data, and further, the step of storing the light intensity data obtained by removing the regions where no signal indicating light from each light-emitting particle in time series light intensity data exists from time series light intensity data into a storage device may be executed by the computer.

Furthermore, also in the above-mentioned computer readable storage device, in the step of removing regions where no signal indicating light from each light-emitting particle exists from the time series light intensity data, at characteristic value of the light intensity which shows the presence or absence of the light from a light-emitting particle in every time section of a predetermined width in the time series light intensity data may be computed out; a time section where no signal indicating light from each light-emitting particle exists may be determined with the characteristic value; and the region corresponding to the time section where no signal indicating light from each light-emitting particle exists may be removed from time series light intensity data. For such a characteristic value of the light intensity showing the presence or absence of light from a light-emitting particle, concretely, either of the integrated value of light intensities, the center value of light intensities, the average of light intensities, the standard deviation of light intensities, the variance of light intensities, the entropy of light intensities, the maximum of light intensities and the particle count computed from the value of the autocorretation function of light intensities when the correlation time is set to 0 in a time section of a predetermined width may be employed. Especially, when the time series light intensity data is time series photon count data, the characteristic value of light intensity may be a value selected from a group of the total sum of photon counts, the center value of photon counts, the average of photon counts, the standard deviation of photon counts, the variance of photon counts, the entropy of photon counts, the maximum of photon counts and the particle count computed from the value of the autocorrelation function of photon counts when the correlation time is set to 0 in a time section of a predetermined width.

Moreover, also in the above-mentioned computer readable storage device, the individual detection of a signal indicating light from each light-emitting particle may be performed based on the shape of the time series signal. In one embodiment, typically, it may be detected that one light-emitting particle entered into the light detection region when a signal having a larger intensity than a predetermined threshold value is detected. The moving speed of the position of the light detection region in the sample solution may be appropriately changed based on the characteristic or the number density or concentration of the light-emitting particle in the sample solution, and preferably, the moving speed of the position of the light detection region in the sample solution may be set to be higher than the diffusional moving velocity of a light-emitting particle. The moving of the position of the light detection region may be done in an arbitrary way, and preferably, the position of the light detection region may be changed by changing the optical path of the optical system of the microscope, or by moving the position of the sample solution. The movement track of the position of the light detection region may be set arbitrarily, for example, which is selectable from circular, elliptical, rectangular, straight and curvilinear ones.

Also in this computer readable storage device, there may be comprised a step of counting the number of the light-emitting particles detected during the moving of the position of the light detection region by counting the number of the signals from the light-emitting partides detected individually and/or a step of determining the number density or concentration of the light-emitting particle in the sample solution based on the number of the detected light-emitting particles.

According to the above-mentioned inventive device or computer readable storage device, there is realized a novel optical analysis method of detecting light of each light-emitting particle with moving the position of a light detection region in a sample solution, in which method, the reduction of the size of light intensity data is possible. Accordingly, according to the present invention, an optical analysis method of detecting light from a light-emitting particle dispersed and moving at random in a sample solution using an optical system of a confocal microscope or a multiphoton microscope, characterized by comprising steps of: moving a position of a light detection region of the optical system of the microscope in the sample solution; detecting intensity of light from the light detection region during moving the position of the light detection region in the sample solution and generating time series light intensity data; and detecting a signal indicating light from the light-emitting particle individually on the time series light intensity data, wherein the method further comprises a step of removing from the time series light intensity data regions where no signal indicating light from each light-emitting particle in the time series light intensity data exists. In this method, typically, in the step of detecting the light from the light detection region and generating the time series light intensity data, the light from the light detection region is detected by photon counting, and in that case, the time series light intensity data is time series photon count data. Also, in the above-mentioned method, in the step of detecting individually a signal indicating light from each light-emitting particle the in time series light intensity data, the signal indicating light from each light-emitting particle may be individually detected on a light intensity data obtained by removing the regions where no signal indicating light from each light-emitting particle in time series light intensity data exists from time series light intensity data, and further, the step of storing the light intensity data obtained by removing the regions where no signal indicating light from each light-emitting particle in time series light intensity data exists from time series light intensity data into a storage device may be conducted.

Furthermore, also in the above-mentioned method, in the step of removing regions where no signal indicating light from each light-emitting particle exists from the time series light intensity data, a characteristic value of the light intensity which shows the presence or absence of the light from a light-emitting particle in every time section of a predetermined width in the time series light intensity data may be computed out; a time section where no signal indicating light from each light-emitting particle exists may be determined with the characteristic value; and the region corresponding to the time section where no signal indicating light from each light-emitting particle exists may be removed from time series light intensity data. For such a characteristic value of the light intensity showing the presence or absence of light from a light-emitting particle, concretely, either of the integrated value of light intensities, the center value of light intensities, the average of light intensities, the standard deviation of light intensities, the variance of light intensities, the entropy of light intensities, the maximum of light intensities and the particle count computed from the value of the autocorrelation function of light intensities when the correlation time is set to 0 in a time section of a predetermined width may be employed. Especially, when the time series light intensity data is time series photon count data, the characteristic value of light intensity may be a value selected from a group of the total sum of photon counts, the center value of photon counts, the average of photon counts, the standard deviation of photon counts, the variance of photon counts, the entropy of photon counts, the maximum of photon counts and the particle count computed from the value of the autocorrelation function of photon counts when the correlation time is set to 0 in a time section of a predetermined width.

Moreover, also in the above-mentioned method, the individual detection of a signal indicating light from each light-emitting particle may be performed based on the shape of the time series signal. In one embodiment, typically, it may be detected that one light-emitting particle entered into the light detection region when a signal having a larger intensity than a predetermined threshold value is detected. The moving speed of the position of the light detection region in the sample solution may be appropriately changed based on the characteristic or the number density or concentration of the light-emitting particle in the sample solution, and preferably, the moving speed of the position of the light detection region in the sample solution may be set to be higher than the diffusional moving velocity of a light-emitting particle. The moving of the position of the light detection region may be done in an arbitrary way, and preferably, the position of the light detection region may be changed by changing the optical path of the optical system of the microscope, or by moving the position of the sample solution. The movement track of the position of the light detection region may be set arbitrarily, for example, which is selectable from circular, elliptical, rectangular, straight and curvilinear ones.

Also in the above-mentioned method, there may be comprised a step of counting the number of the light-emitting particles detected during the moving of the position of the light detection region by counting the number of the signals from the light-emitting particles detected individually and/or a step of determining the number density or concentration of the light-emitting particle in the sample solution based on the number of the detected light-emitting particles.

The optical analysis technique of the above-mentioned present invention is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention, also.

Effect of Invention

Generally, according to the inventive optical analysis technique, by reducing the size of light intensity data through deleting selectively regions where no signals of light-emitting particles exist in time series light intensity data in the scanning molecule counting method, the reduction of the load and processing time in analysis processing of these light intensity data and the saving of the memory volume for memorizing the data are achieved. As explained in detail in the below-mentioned column of the explanation of embodiments, especially in accordance with the manner of determining time sections where no signals of light-emitting particles exist using a characteristic value of the light intensity indicating the presence or absence of light from light-emitting particles computed in every time section of a predetermined width in the time series light intensity data and removing from the time series light intensity data the regions corresponding to the time sections where no signal indicating light from each light-emitting particle exists, it becomes possible to compress data volume to about $1/10$ in some conditions. Thus, according to the present invention, the reduction of the size of light intensity data is possible, and the reduction of the memory capacity of a storage device necessary for storing data and the reduction of calculating capacity necessary for analysis processing are attained so that the cost required for conducting the scanning molecule counting method can be saved, and therefore, the expansion of the use opportunity of the scanning molecule counting method will be expected.

Other purposes and advantages of the present inventions will become clear by explanations of the following preferable embodiments of the present invention.

BRIEF DESCRIPTIONS OF DRAWINGS

FIG. 1A is a schematic diagram of the internal structure of the optical analysis device with which the inventive method is performed. FIG. 1B is a schematic diagram of a confocal volume (an observation region of a confocal microscope). FIG. 1C is a schematic diagram of the mechanism for changing the direction of the mirror 7 to move the position of a light detection region in a sample solution. FIG. 1D is a schematic diagram of the mechanism for moving the position of the light detection region in a sample solution by moving the horizontal position of the micro plate.

FIGS. 2A and 2B are a schematic diagram explaining the principle of the light detection and a schematic diagram of the variation of the measured light intensity with time in the scanning molecule counting method to which the inventive method is applied, respectively. FIG. 2C is a drawing which explains about the principle in a case of detecting a signal of a light-emitting particle after deleting regions where no signals of light-emitting particles exist from time series light intensity data. FIG. 2D is a drawing explaining about the principle in the case of deleting regions where no signals of light-emitting particles exist from time series light intensity data after performing the detection of signals of light-emitting particles.

FIGS. 3A and 3B are diagrams showing the procedures of the scanning molecule counting method performed in accordance with the inventive method in the form of a flow chart. FIG. 3C is a diagram showing one example of the ways of detecting a signal of a light-emitting particle individually on light intensity data in the form of a flow chart.

FIGS. 4A and 4B are drawings of models in a case that a light-emitting particle crosses a light detection region owing to the Brownian motion and in a case that a light-emitting particle crosses a light detection region by moving the position of the light detection region in a sample solution at a velocity quicker than the diffusional moving velocity of the light-emitting particle. FIG. 4C shows drawings explaining an example of the signal processing step of the detected signals in the procedure for detecting the existence of a light-emitting particle from the measured time series light intensity data (change in time of photon count) in accordance with the scanning molecule counting method.

FIG. 5 shows examples of measured photon count data (bar graph); curves obtained by carrying out the smoothing of the data (dotted line); and Gauss functions fitted on the pulse existing region (solid line). In the drawing, the signals attached with "noise" are disregarded as signals due to noises or a contaminant.

The upper row of FIG. 6A is an example of time series data of the light intensity (photon count) obtained with the light detector, and the lower row of FIG. 6A is an enlarged view showing a part of the start of the upper row. The upper row of FIG. 6B is an example of the light intensity data obtained by carrying out the digesting process of the time series light intensity data of FIG. 6A, and the lower row is an enlarged view showing a part of the start of the upper row. For the measurement conditions of light intensity, see text. The digesting process was made with the window size of 200 μseconds, and the threshold value of the characteristic value (the sum of photon counts) of 5. In the drawing, the round dotted line shows the threshold value (one photon count) for detection of a signal of a light-emitting particle.

Figure 9A:
Figure 9A:
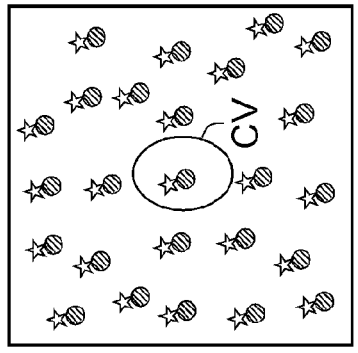
Figure 9B:
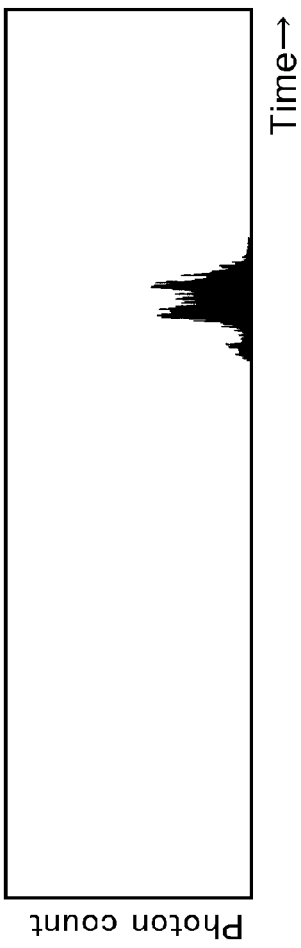
Figure 9B:
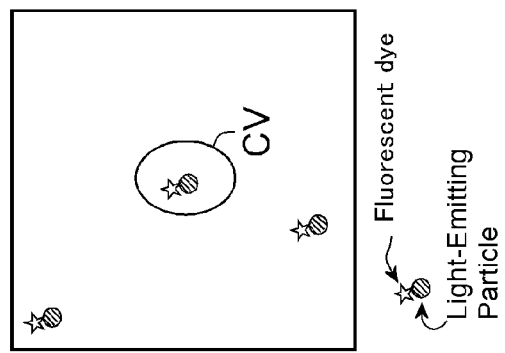

FIG. 9 show examples of the time variation of the photon count (light intensity) obtained in a conventional optical analysis technique computing fluorescence intensity fluctuation, where FIG. 9A shows a case that the particle concentration is at a level providing a sufficient precision in the measurement, and FIG. 9B shows a case that the particle concentration in a sample is significantly lower than the case of FIG. 9A.

EXPLANATIONS OF REFERENCE NUMERALS

1 - - -Optical analysis device (confocal microscope)
2 - - -Light source
3 - - -Single mode optical fiber
4 - - -Collimating lens
5 - - -Dichroic mirror
6, 7, 11 - - -Reflective mirror
8 - - -Objective
9 - - -Micro plate
10 - - -Well (sample solution container)
12 - - -Condenser lens
13 - - -Pinhole
14 - - -Barrier filter
15 - - -Optical fiber
16 - - -Photodetector
17 - - -Mirror deflector
17a - - -Stage position changing apparatus
18 - - -Computer
Description Of Embodiments
In the followings, preferable embodiments of the present invention are described in detail.

Structure of Optical Analysis Device

In the basic structure, an optical analysis device which realizes the optical analysis technique according to the present invention may be a device constructed by associating the optical system of a confocal microscope and a photodetector, enabling FCS, FIDA, etc., as schematically illustrated in FIG. 1A. Referring to this drawing, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light, emitted from a light source 2 and transmitted through the inside of a single mode fiber 3 (Ex), forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are typically fluorescent molecules or particles to which a light emitting label such as a fluorescent dye is attached, are dispersed or dissolved, and when such a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13 and penetrates through the barrier filter 14 (where a light component only in a specific wavelength band is selected); and is introduced into a multimode fiber 15, reaching to the photodetector 16, and after the conversion into time series electric signals, the signals are inputted into the computer 18, where the processes for optical analyses are executed in manners explained later. In this regard, as known in ones skilled in the art, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the excitation region is blocked. The focal region of the laser light illustrated in FIG. 1B is a light detection region, whose effective volume is usually about 1-10 fL in this optical analysis device (typically, the light intensity is spread in accordance with a Gaussian distribution having the peak at the center of the region. Its effective volume is a volume of an approximate ellipsoid bordering a surface where the light intensity is reduced to $1/e^2$ of the peak intensity.), which focal region is called as "confocal volume". Further, since, in the present invention, the light from one light-emitting particle, for example, the faint light from one fluorescent dye molecule, is detected, a super high sensitive photodetector, usable for the photon counting, is preferably used for the photodetector 16. When the detection of light is performed by the photon counting, the measurement of light intensity is performed for a predetermined time in a manner of measuring the number of photons which have sequentially arrived at a photodetector in every predetermined unit time (BIN TIME). Thus, in this case, the time series light intensity data is time series photon count data. In addition, in order to change the well 10 to be observed, the stage (not shown) of the microscope may be provided with a stage position changing apparatus 17a for moving the horizontal position of the micro plate 9. The operation of the stage position changing apparatus 17a may be controlled by the computer 18. According to this structure, quick measurements become achievable even when there are two or more specimens.

Furthermore, in the optical system of the above-mentioned optical analysis device, there is further provided a mechanism for scannig the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C (mode of moving the absolute position of the light detection region). This mirror deflector 17 may be the same as that of a galvanomirror device equipped on a usual laser scan type microscope. Or, as an alternative manner, as illustrated in FIG. 1D, the stage position changing apparatus 17a may be operated to move the horizontal position of the container 10 (microplate 9) into which the sample solution has been dispensed for moving the relative position of the light detection region in the sample solution (mode of moving the absolute position of the sample solution). In either of the ways, in order to attain a desired moving pattern of the position of the light detection region, the mirror deflector 17 or the stage position changing apparatus 17a is driven in harmony with the light detection of the photodetector 16 under the control of the computer 18. The movement track of the position of the light detection region may be arbitrarily selected from circular, elliptical, rectangular, straight and curvilinear ones, or a combination of these (The program in the computer 18 may be designed so that various moving patterns can be selected.). In this regard, although not illustrated, the position of the light detection region may be moved in the vertical direction by moving the objective 8 or the stage up and down.

In the case that a light-emitting particle to be an object to be observed emits light by multiple photon absorption, the above-mentioned optical system is used as a multiphoton microscope. In that case, since the light is emitted only from the focal region of the excitation light (light detection region), the pinhole 13 may be removed. Further, in the case that a light-emitting particle to be an object to be observed emits light owing to a chemiluminescence or bioluminescence phenomenon without excitation light, the optical system 2-5 for generating excitation light may be omitted. When a light-emitting particle emits light owing to phosphorescence or scattered light, the above-mentioned optical system of the confocal microscope is used as it is. Furthermore, in the optical analysis device 1, as shown in the drawing, two or more excitation light sources 2 may be provided so that the wavelength of the excitation light can be appropriately selected in accordance with the wavelength of the light for exciting a light-emitting particle. Similarly, two or more photodetectors 16 may also be provided so as to detect the lights from light-emitting particles of two or more kinds having different light-emitting wavelengths, if contained in a sample, separately, depending upon the wavelengths. The computer 18 has performs a CPU and a memory, and the inventive procedures are performed through the CPU executing various operational processings. In this regard, each procedure may be done with hardware. All or a part of processes explained in this embodiment may be performed by the computer 18 with a computer readable storage device having memorized the programs to realize those processes. Accordingly, the computer 18 may read out the program memorized in the storage device and realize the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program.

The Principle of the Inventive Optical Analysis Technique

As described in the column of "Summary of Invention", briefly, in the inventive optical analysis technique, reduction of the size of time series light intensity data (digesting process) is performed. In the following, the principles of the scanning molecule counting method and the digesting process of time series light intensity data of the present invention are explained.

1. Principle of Scanning Molecule Counting Method

Spectral analysis techniques, such as FCS, FIDA, etc., are advantageous in that the required sample amount is extremely small and a test can be performed promptly as compared with the conventional biochemical analytical techniques. However, in these spectral analysis techniques, such as FCS, FIDA, etc., the concentration and characteristics of a light-emitting particle are principally computed based on the fluorescence intensity fluctuation, and therefore, in order to obtain accurate measurement results, the concentration or number density of the light-emitting particle in a sample solution should be at a level where about one light-emitting particle always exists in a light detection region CV during the fluorescence intensity measurement as schematically drawn in FIG. 9A so that significant light intensity (photon count) can be always detected in the measuring term as shown in the right-hand side of the drawing. When the concentration or number density of the light-emitting particle is lower than that, for example, at the level where the light-emitting particle rarely enters into the light detection region CV as drawn in FIG. 9B, no significant light intensity signal (photon count) would appear in a part of the measuring term as illustrated on the right-hand side of the drawing, and thus, accurate computation of light intensity fluctuation would become difficult. Also, when the concentration of the light-emitting particle is significantly lower than the level where about one light-emitting particle always exists in the inside of the light detection region during the measurement, the calculation of light intensity fluctuation would become subject to the influence of the background, and the measuring time should be made long in order to obtain the significant quantity of the light intensity data (photon count) sufficient for the calculation.

Then, in the Japanese patent application no. 2010-044714, and PCT/JP2011/53481, the applicant of the present application has proposed "Scanning molecule counting method" based on a new principle which enables the detection of characteristics of a light-emitting particle, such as its number density or concentration, even when the concentration of the light-emitting particle is lower than the level requested in the above-mentioned spectral analysis techniques, such as FCS and FIDA.

Figure 2A:
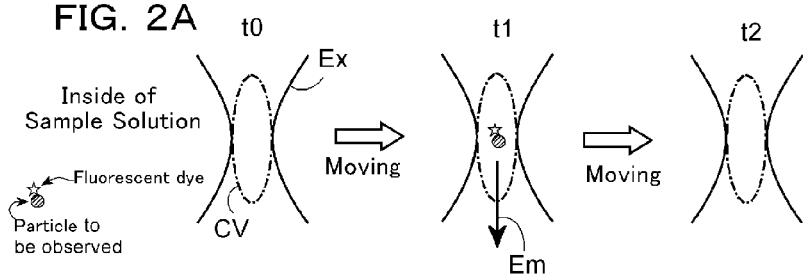
Figure 2B:
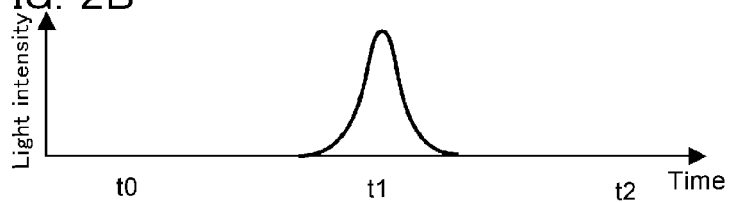

As the processes to be performed in the scanning molecule counting method, briefly speaking, the light detection is performed together with moving the position of the light detection region CV in a sample solution, namely, scanning the inside of the sample solution with the light detection region CV by driving the mechanism (mirror deflector 17) for moving the position of the light detection region to change the optical path as schematically drawn in FIG. 2A. Then, for example, during the moving of the light detection region CV (in the drawing, time to-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. In the principle of the scanning molecule counting method, no statistical calculation processes, such as the calculation of the fluorescence intensity fluctuation, are conducted and the light-emitting particles are one by one detected, and therefore, the information about the concentration or number density of the particle is acquirable even in a sample solution with a low particle concentration at the level where no sufficiently accurate analysis is available in FCS, FIDA, etc.

2. Principle of Digesting Process of Time Series Light Intensity Data

As already noted, in the data of the light intensity temporally acquired by the above-mentioned scanning molecule counting method with the photodetector 16 (time series light intensity data), the regions where the signals of light-emitting particle exist are only parts of all the regions, and in the regions on which no signals of light-emitting particles exist, there exist only noises made caused by heat noise of the photodetector, background light, etc. Then, in the present invention, the reduction of the size of time series light intensity data is achieved through removing regions in the time series light intensity data where no signals of light-emitting particles exist, from the time series light intensity data. In this regard, in the present specification, the reducing process of the size of time series light intensity data is called "digesting process" in the followings.

(i) A Case that a Signal of a Light-Emitting Particle is Detected after the Digesting Process In one manner of the digesting process of time series light intensity data, regions where no signals of light-emitting particles exist are detected on time series light intensity data; the light intensity data obtained by removing these regions from the time series light intensity data (digested light intensity data) are prepared; and the individual detection of a signal of a light-emitting particle is performed on the digested light intensity data. Concretely, in order to distinguish between a region where a signal of a light-emitting particle exists and a region where no signals of light-emitting particles exist, first, as shown in the upper row of FIG. 2C, a characteristic value of the light intensity showing the presence or absence of the light from a light-emitting particle is computed in every time section of a predetermined width on time series light intensity data, using the light intensity values (photon counts) in each time section (e.g. in every respective region A-D). As already noted, in the time series light intensity data, as pulse form signal exists in the region in which the signal of a light-emitting particle exists while there are only noises in a region where no signals of light-emitting particles exist, and thus, the region where the signal of a light-emitting particle exists and the region where no signals of light-emitting particles exist have mutually different characteristics in light intensity values. Accordingly, it is possible to compute an arbitrary characteristic value of the light intensity indicating the presence or absence of the light from a light-emitting particle in every time section of a predetermined width on time series light intensity data, and determine time sections corresponding to regions where no signals of light-emitting particles exist based on the characteristic values.

As the characteristic value of the light intensity indicating the presence or absence of the light from a light-emitting particle, an arbitrary value whose magnitude in a time section of a predetermined width where light from a light-emitting particle exists becomes larger than the magnitude in a time section of the predetermined width where no light from a light-emitting particle exists is employable. In that case, when the characteristic value of the light intensity is larger than a predetermined threshold value, it is judged that a signal from a light-emitting particle exists in the time section of the predetermined width. Such a characteristic value may be, for example, either of the integrated value of light intensities, the center value of light intensities, the average of light intensities, the standard deviation of light intensities, the variance of light intensities, the entropy of light intensities, the maximum of light intensities and the particle count computed from the value of the autocorrelation function of light intensities when the correlation time is set to 0 in a time section of a predetermined width. In this regard, typically, the light detector detects the light from the light detection region by photon counting, and in this case, the time series light, intensity data is time series photon count data. Accordingly, the characteristic value of light intensity may be a value selected from a group of the total sum of photon counts, the center value of photon counts, the average of photon counts, the standard deviation of photon counts, the variance of photon counts, the entropy of photon counts, the maximum of photon counts and the particle count computed from the value of the autocorrelation function of photon counts when the correlation time is set to 0 in a time section of a predetermined width. (In FIG. 2C, the total sum of the photon counts in each time section is employed as the characteristic value.).

Figure 2C:
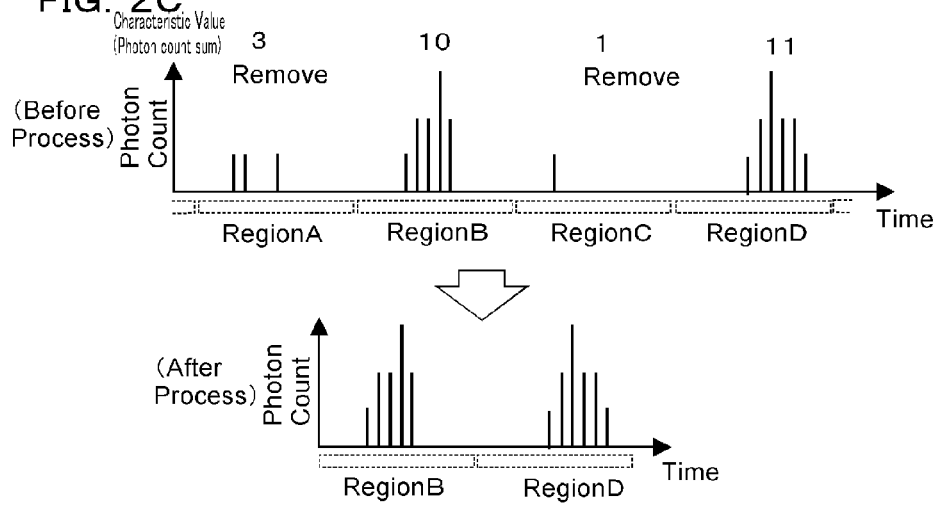

Then, when the characteristic value in each time section is determined, with reference to this characteristic value, for instance, with reference to whether or not the characteristic value exceeds beyond a predetermined threshold value, it is determined in each time section whether or not a signal of a light-emitting particle exists; the region(s) (in the drawing, the regions B and D) corresponding to the time section(a) where a signal of a light-emitting particle exists is (are) extracted selectively; and as in the lower row of FIG. 2C, there are prepared the digested light intensity data where the region(s) (In the drawing, the regions A and C) corresponding to the time section(s) where no signals of light-emitting particles exist has (have) been removed. And next, the signal of a light-emitting particle is detected on the so prepared, digested light intensity data in a manner as explained in detail later. According to this manner, since the size of the data to be processed in the detection processing of a signal of a light-emitting particle becomes small, and it becomes unnecessary to carry out data processing for unnecessary regions, the reduction of the load and processing time in the data processing is expected. Also, in the storing of the measured data into a storage device, the saving of the memory volume of the storage device can be achieved through storing the digested light intensity data.

In this regard, in the above-mentioned process, the predetermined width of a time section and the threshold value for a characteristic value may be set arbitrarily. However, as explained in Embodiment section later, the accuracy in detecting a signal of a light-emittitig particle and the data compressibility (the size of the digested light intensity data/ the size of the time series light intensity data) vary depending upon the setting of the predetermined width of the time section and the threshold value for the characteristic value, and thus, it is preferable to set appropriate values using results of preliminary experiments, etc.

(ii) A case that the Digesting Process is Performed after Detection of Light-Emitting Particle Signal(s)

Figure 2D:
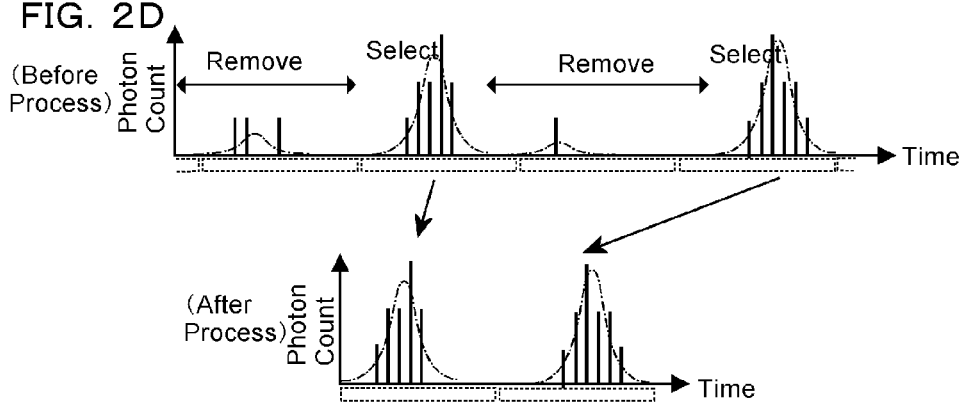

In another manner of the digesting process of time series light intensity data first, as schematically shown in the upper row of FIG. 2D, after performing detection of a signal of a light-emitting particle on time series light intensity data by the process, etc. including, for example, the fitting process of a bell shaped function (as described later), the digested light intensity data are prepared by removing the regions corresponding to the time sections where no signals of light-emitting particles exist and selecting only the regions corresponding to the time sections where a signal of a light-emitting particle exists (see FIG. 2D). In this case, although the load and processing time for the detection processing of a signal of a light-emitting particle become larger rather than in the case of (i), the saving of the memory volume of a storage device can be archived by selecting the digested light intensity data as the data to be stored. Since the predetermined width of a time section influences the data compressibility, it is preferable to set an appropriate value using results of a preliminary experiment, etc. (see embodiment described below).

Operation Processes of Scanning Molecule Counting

Figure 3A:
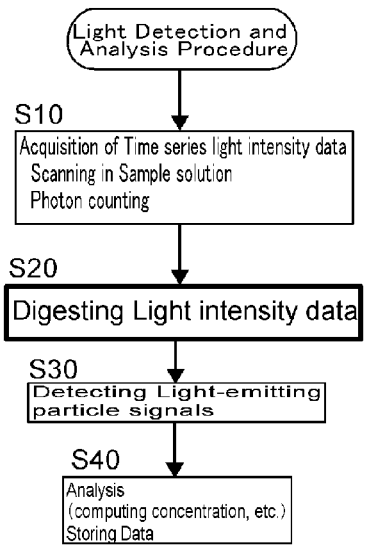
Figure 3B:
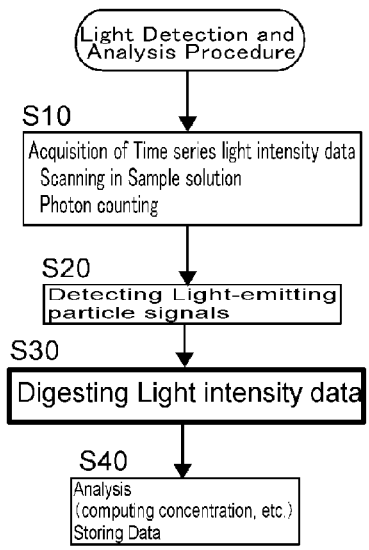
Figure 3C:
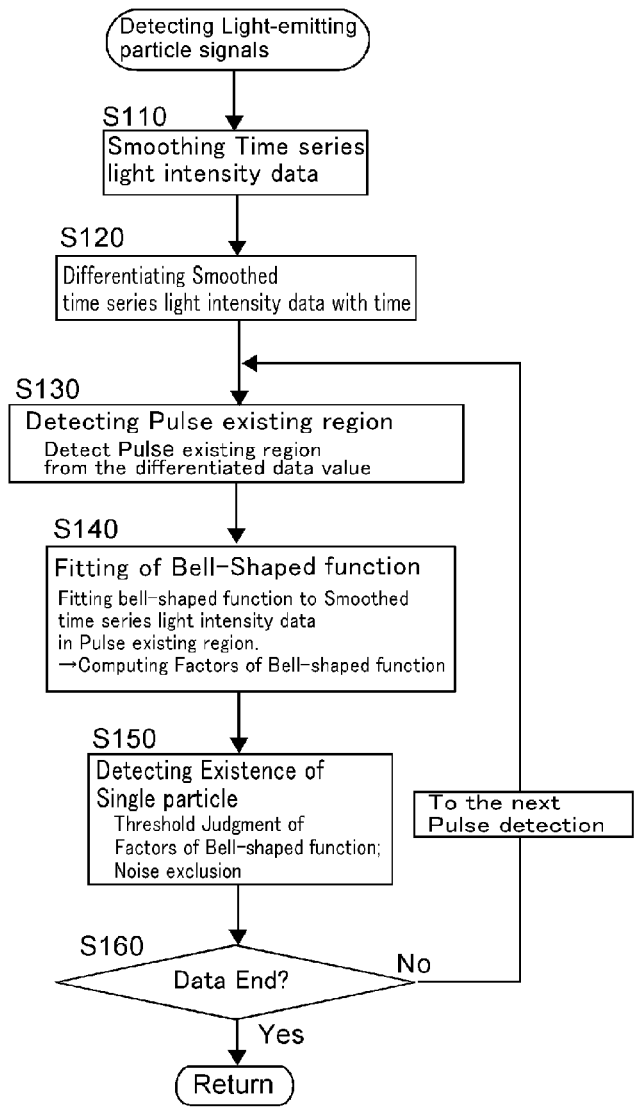

In the embodiment of the scanning molecule connting method in accordance with the present invention with the optical analysis device 1 as illustrated in FIG. 1A, concretely, there are conducted (1) preparation of a sample solution containing light-emitting particles; (2) process of measuring the light intensity of the sample solution and (3) process of analyzing measured light intensities. FIG. 3 shows the processes in this embodiment in form of the flow chart. In this regard, FIG. 3A shows the processes in the case of detecting a signal of a light-emitting particle after the digesting process, and FIG. 3B shows the processes in the case of performing the digesting process after detection of signal(s) of light-emitting particle(s). In addition, FIG. 3C shows an example of the detection process of a signal of a light-emitting particle.

(1) Preparation of a Sample Solution

The article to be an observed object in the inventive optical analysis technique may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological molecule. In a case that the particle to be an observed object is not a particle which emits light, a particle to which a light emitting label (a fluorescence molecule, a phosphorescence molecule, and a chemiluminescent or bioluminescent molecule) is attached in an arbitrary manner is used. The sample solution is typically an aqueous solution, but not limited to this, and it may be an organic solvent or other arbitrary liquids.).

(2) Measurement of the Light Intensity of a Sample Solution (FIG. 3A, 3B step 10)

The measurement of the light intensity in the optical analysis by the scanning molecule counting method of the present embodiment may be performed in a manner similar to the measurement process of the light intensity in FCS or FIDA, except that driving the mirror deflector 17 or the stage position changing apparatus 17a to move the position of the light detection region in a sample solution (scanning in a sample solution) is conducted during the measurement of light intensity. In the operation processes, typically, after dispensing a sample solution into the well(s) 10 of the micro plate 9 and putting it on the stage of the microscope, when a user inputs to the computer 18 a command of staring a measurement, the computer 18 executes programs memorized in a storage device (not shown) (the process of moving the position of the light detection region in the sample solution, and the process of detecting light from the light detection region during the moving of the position of the light detection region) to start radiating the excitation light and measuring the light intensity in the light detection region. During this measurement, under the control of the operation process of the computer 18 according to the programs, the mirror deflector 17 or the stage position changing apparatus 17a drives the mirror 7 (galvanomirror) or the micro plate 9 on the stage of the microscope to move the position of the light detection region in the well 10, and simultaneously with this, the photodetector 16 sequentially converts the detected light into an electric signal and transmits it to the computer 18, in which the time series light intensity data is generated from the transmitted signals and stored it in an arbitrary manner. In this connection, the photodetector 16 is typically a super high sensitive photodetector which can detect an arrival of a single photon, and thus, when the detection of light is performed by the photon counting, the time series light intensity data may be time series photon count data.

The moving speed of the position of the light detection region during the measurement of the light intensity may he a predetermined velocity set arbitrarily, for example, experimentally or in order to meet the purpose of an analysis. In a case of acquiring the information on the number density or concentration based on the number of detected light emitting particles, the region size or volume through which the light detection region has passed is required, and therefore, the moving of the position of the light detection region is performed in it manner enabling the grasping of the moving distance. In this regard, because the interpretation of a measurement result will become easy if the elapsed time is proportional to the moving distance of the position of the light detection region, basically, it is preferable that the moving speed is constant, although not limited thereto.

Figure 4A:
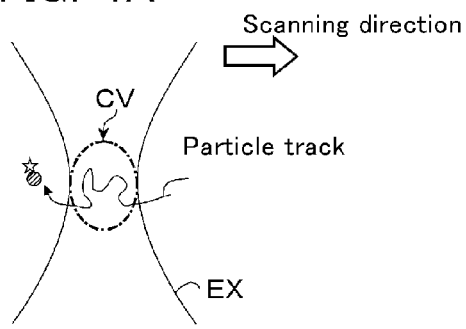

By the way, regarding the moving speed of the position of the light detection region, in order to perform quantitatively precisely individual detection of a light-emitting particle to be observed from the measured time series light intensity data or the counting of the number of light-emitting particles, it is preferable that the moving speed is set to a value quicker than the moving speed in the random motion, i.e., Brownian motion of a light-emitting particle. Since the particle to be the observation object in the inventive optical analysis technique is a particle dispersed or dissolved in a solution and moving at random freely, its position moves time owing to the Brownian motion. Thus, when the moving speed of the position of the light detection region is slower than the movement of a particle owing to the Brownian motion, the particle moves at random in the region as schematically drawn in FIG. 4A, whereby the light intensity changes at random (as noted, the excitation light intensity in the light detection region is reduced from the peak at the center of the region toward its outside.), so that it becomes difficult to determine a significant light intensity change corresponding to each light-emitting particle. Then, preferably, as drawn in FIG. 4B, the moving speed of the position of the light detection region is set to be quicker than the average moving speed of a particle by the Brownian motion (diffusional moving velocity) so that the particle will cross the light detection region in an approximately straight line and thereby the profile of the change of the light intensity corresponding to each light-emitting particle becomes almost uniform in the time series light intensity data as illustrated in the most upper row of FIG. 4C (When a light-emitting particle passes through the light detection region in an approximately straight line, the profile of the light intensity change is similar to the excitation light intensity distribution.) and the correspondence between each light-emitting particle and light intensity can be easily determined.

Coneretely, the time $\Delta t$ irequired for a light-emitting particle having a diffusion coefficient D to pass through the light detection region of radius Wo (confocal volume) by the Brownian motion is given from Expression of the relation of mean-square displacement:

$$(2Wo)^2 = 6D \cdot \Delta t \quad (1)$$

as:

$$\Delta t = (2Wo)^2/6D \quad (2),$$

and thus, the velocity of the light-emitting particle moving by the Brownian motion (diffusional moving velocity) Vdif, becomes approximately $$V\text{dif} = 2Wo/\Delta t = 3D/Wo \quad (3)$$

Then, with reference to this, the moving speed of the position of the light detection region may be set to a value sufficiently quicker than Vdif. For example, when the diffusion coefficient of a particle to be observed is expected to be about $D = 2.0 \times 10^{-10}$ m$^2$/s, Vdif will be $1.0 \times 10^{-3}$ m/s, supposing Wo is about 0.62 μm, and therefore, the moving speed of the position of the light detection region may be set to its 10 times or more, 15 mm/s. In this regard, when the diffusion coefficient, of a particle to be observed is unknown, an appropriate moving speed of the position of the light detection region may be determined by repeating the executions of a preliminary experiment with setting various moving speeds of the position of the light detection region in order to find the condition that the profile of a light intensity variation becomes an expected profile (typically, similar to the excitation light intensity distribution).

(3) Analysis of Light Intensity

After the time series light intensity data has been obtained by the above-mentioned processes, various analyses, such as the detection of signals of light-emitting particles, the counting of the light-emitting particles, the calculation of its concentration are performed in the computer 18 through processes according to programs memorized in a storage device. Further, as already noted, especially in the present invention, the digesting process of time series light intensity data is performed before or after the detection of signals of light-emitting particles. Hereafter, (i) the case of performing the digesting process before detection of signals of light-emitting particles (FIG. 3A) and (ii) the case of performing the digesting process after detection of signals of light-emitting particles (FIG. 3B) are explained, respectively.

(i) The Case of Performing the Digesting Process Before Detection of Signals of Light-Emitting Particles (a) Digesting Process (FIG. 3A step 20)

In the digesting process of the case of performing the digesting process before detection of signals of light-emitting particles, as already noted, the characteristic value of the light intensity is computed for every time section of a predetermined width in the time series light intensity data obtained in Step 10. For the characteristic value of light intensity, it may be a value selected from a group of the total sum of photon counts, the center value of photon counts, the average of photon counts, the standard deviation of photon counts, the variance of photon counts, the entropy of photon counts, the maximum of photon counts and the particle count computed from the value of the autocorrelation function of photon counts when the correlation time is set to 0 in a time section of a predetermined width.

Regarding the respective characteristic values, more in details, the total sum of photon counts is the total value of photon counts in a time section of a predetermined width. Since the total sum of a time section where (a) signal(s) of (a) light-emitting particle(s) exist(s) increases by the photon counts from the light-emitting particle(s) larger than the total values of other time sections, when the magnitude of the total sum of a certain time section is larger than a predetermined threshold value, it is judged that (a) signal(s) of (a) light-emitting particle(s) exist(s) in the certain time section.

The center value and the maximum of photon counts are the center value and the maximum of the photon counts found out in a time section of a predetermined width, respectively. Since, usually, a photon count during a period when the light of a light-emitting particle has arrived at a photodetector becomes larger than cases where only noises occur, the center value and the maximum of a time section where (a) signal(s) of (a) light-emitting particles exist(s) increase, also. Thus, when the magnitude of the center value or the maximum of a certain time section is larger than a predetermined threshold value, it is judged that (a) signal(s) of (a) light-emitting-particle(s) exist(s) in the certain time section.

The average of photon counts is the time average value of photon counts in a time section of a predetermined width. As noted above, since the total sum in a time section where (a) signal(s) of (a) light-emitting particle(s) exists increases by the photon count from the light-emitting particle(s) larger than the total sum value of other time sections, the time average value of the photon counts in the time section of a predetermined width also increases. Thus, when the magnitude of the average value of a certain time section is larger than a predetermined threshold value, it is judged that (a) signal(s) of (a) light-emitting particle(s) exist(s) in the certain time section.

The standard deviation values, variance value and entropy value of photon counts each are the standard deviation value and the variance value in the time average of the photon counts and the entropy value of information amounts in a time section of a predetermined width, and these are characteristic values indicating the degree of scatterings in the time changes of photon counts found out in the time section of the predetermined width. When a signal of a light-emitting particle exists in a certain time section, the time change of the photon count becomes more disturbed as compared with the other time sections. Thus, the standard deviation value, variance value and entropy value of photon counts of the time section where a signal of a light-emitting particle exists increase as compared with the corresponding values in the other time sections, and therefore, it is judged that (a) signal(s) of (a) light-emitting particle(s) exist(s) in a certain time section when each value of the time section is larger than the corresponding predetermined threshold value. In this regard, the entropy value of photon counts is given by:

$$-\log_2 (p0^{i0} \cdot p1^{i1} \cdot \cdots \cdot px^{ix} \cdot \cdots \cdot pn^{in}) \quad (4),$$

when the probability that the photon count at a certain time (BIN TIME) is x pieces is px with the number ix of the time points at which the photon count is x in a certain time section. Usually, the probability px that the photon count is x is give as: $p0 > p1 > p2 > \cdots > px \cdots > pn$. Although the entropy value of a section where only noises exist is $-\log_2 (p0^{i0} \cdot p1^{i1} \cdot p2^{i2})$, etc., it becomes $-\log_2 (p0^{i0} \cdot p1^{i1} \cdot p2^{i2} \cdot p3^{i3} \cdot p4^{i4})$ etc. in a section where a signal of a light-emitting particle exists, and thus the value increases.

The particle count computed from an autocorrelation function value of the photon counts with setting the correlation time to 0 in a time section of a predetermined width is the amount equivalent to the particle count in the time section. According to the theory of FCS, the autocorrelation function of light intensity, C (τ), is given by

[Expression 1]

$$C(\tau) = 1 + \frac{1}{N}\left(1 + \frac{\tau}{\tau_D}\right)^{-1}\left(1 + \frac{\tau}{AR^2\tau_D}\right)^{-1/2} \quad (5)$$

(Here, τD is a translational diffusion time, AR is a structure parameter and N is the particle count.). In the above-mentioned expression, the particle count N is given by 1/(C(0)−1) from C(0) at time of the correlation time τ=0. It is considered that this particle count is a particle count found out in every time section, and thus, when it is larger than predetermined threshold value, it is judged that (a) signal(s) of (a) light-emitting particle(s) exist(s) in the time section, similarly to the above-mentioned characteristic values.

Thus, digested light intensity data, as illustrated in FIG. 2C lower row, is prepared by computing one of the above-mentioned characteristic values in each time section of time series tight intensity data, choosing time sections whose characteristic value exceeds a predetermined threshold value as regions where (a) signal(s) of (a) light-emitting particle(s) exist(s); and identifying and removing time sections whose characteristic value is less than the predetermined threshold value as regions where no signals of light-emitting particles exist.

(b) Individual Detection of a Signal of a Light-Emitting Particle (see FIG. 3A step 30 and FIG. 3C)

Figure 4B:
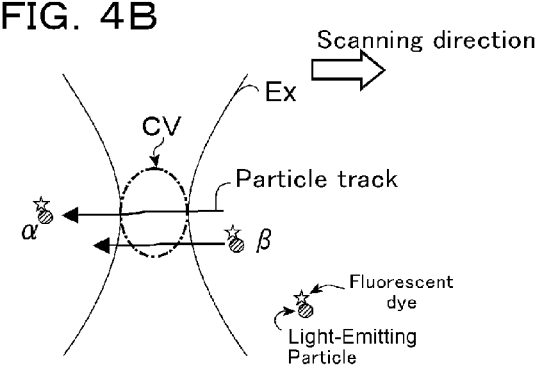

After the preparation of the digested light intensity data by the above-mentioned processes, the process of detecting a signal of a light-emitting particle individually is performed on the light intensity data. As already noted, when the track of one light-emitting particle in its passing through the light detection region is approximately straight as shown in FIG. 4B, the light intensity variation in the signal corresponding to the particle on the time series light intensity data has a bell shaped profile reflecting the light intensity distribution in the light detection region determined by the optical system. Thus, basically in the scanning molecule counting method, when the time width Δτ for which the light intensity value exceeding an appropriately set threshold value Ith continues is in a predetermined range on the light intensity data, the signal having the profile of the light intensity may be judged to correspond to one particle having passed through the light detection region, and thereby one light-emitting particle is detected. And a signal whose light intensity does not exceed the threshold value Ith or which does not have time width Δτ in the predetermined range is judged as noise or a signal of a contaminant. Further, when the light intensity distribution in the light detection region can be assumed as Gaussian distribution:

$$I = A \cdot \exp(-2t^2/a^2) \quad (6),$$

and when the intensity A and the width a, computed by fitting Expression (6) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The signal with the intensity A and the width a out of the predetermined ranges may be judged as a noise or a contaminant signal and ignored in the later analysis, etc.).

Figure 4C:
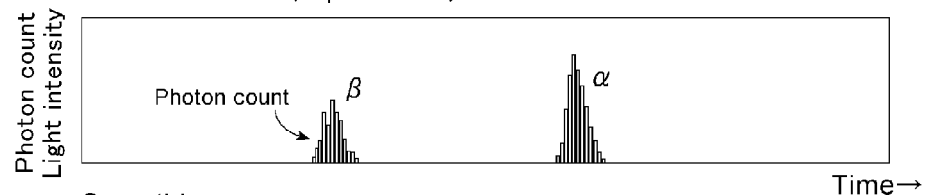
Figure 4C:
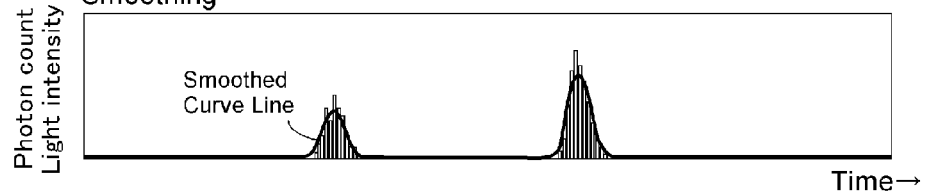
Figure 4C:
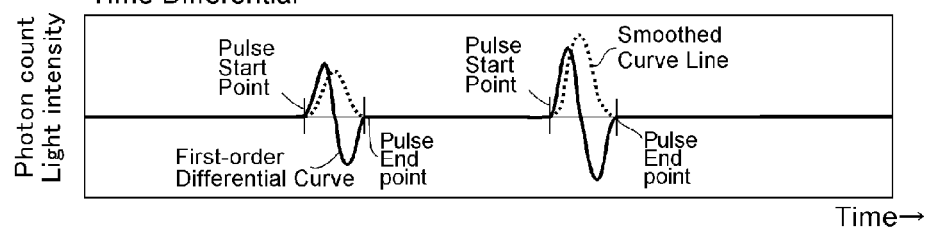
Figure 4C:
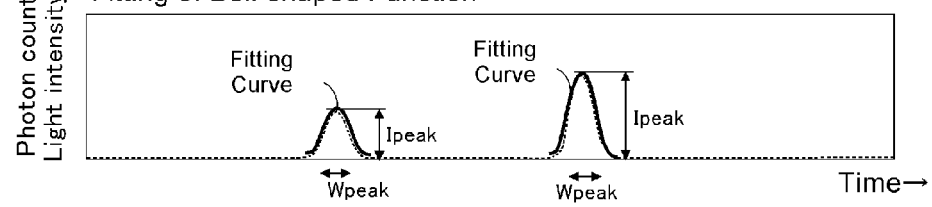

As an example of the process of the detection of signals on light intensity data, first, a smoothing treatment is performed to the time series light signal data (FIG. 4C), the most upper row "detected result (unprocessed)") (FIG. 3C—step 110, FIG. 4C mid-upper row "smoothing"). Although the light emitted by a light-emitting particle is stochastic so that gaps will be generated in data values in minute time, such gaps in the data value can be disregarded by the smoothing treatment. The smoothing treatment may be done, for example, by the moving average method. In this regard, parameters in performing the smoothing treatment, e.g., the number of datum points in one time of the averaging, the number of times of a moving average,. etc, in the moving averages method, may be appropriately set in accordance with the moving speed (scanning speed) of the position of the light detection region and/or BIN TIME in the light intensity data acquisition.

Next, on the light intensity data after the smoothing treatment, in order to detect a time domain (pulse existing region) in which a significant pulse form signal (referred to as "pulse signal" hereafter) exists, the first differentiation value with time of the light intensity data after the smoothing treatment is computed (step 120). As illustrated in FIG. 4C, the mid-low row "time differential", in the time differential value of light signal data, the variation of the value increases at the time of the signal value change, and thereby, the start point and the end point of a significant signal can be determined advantageously by referring to the time differential value.

Figure 5:
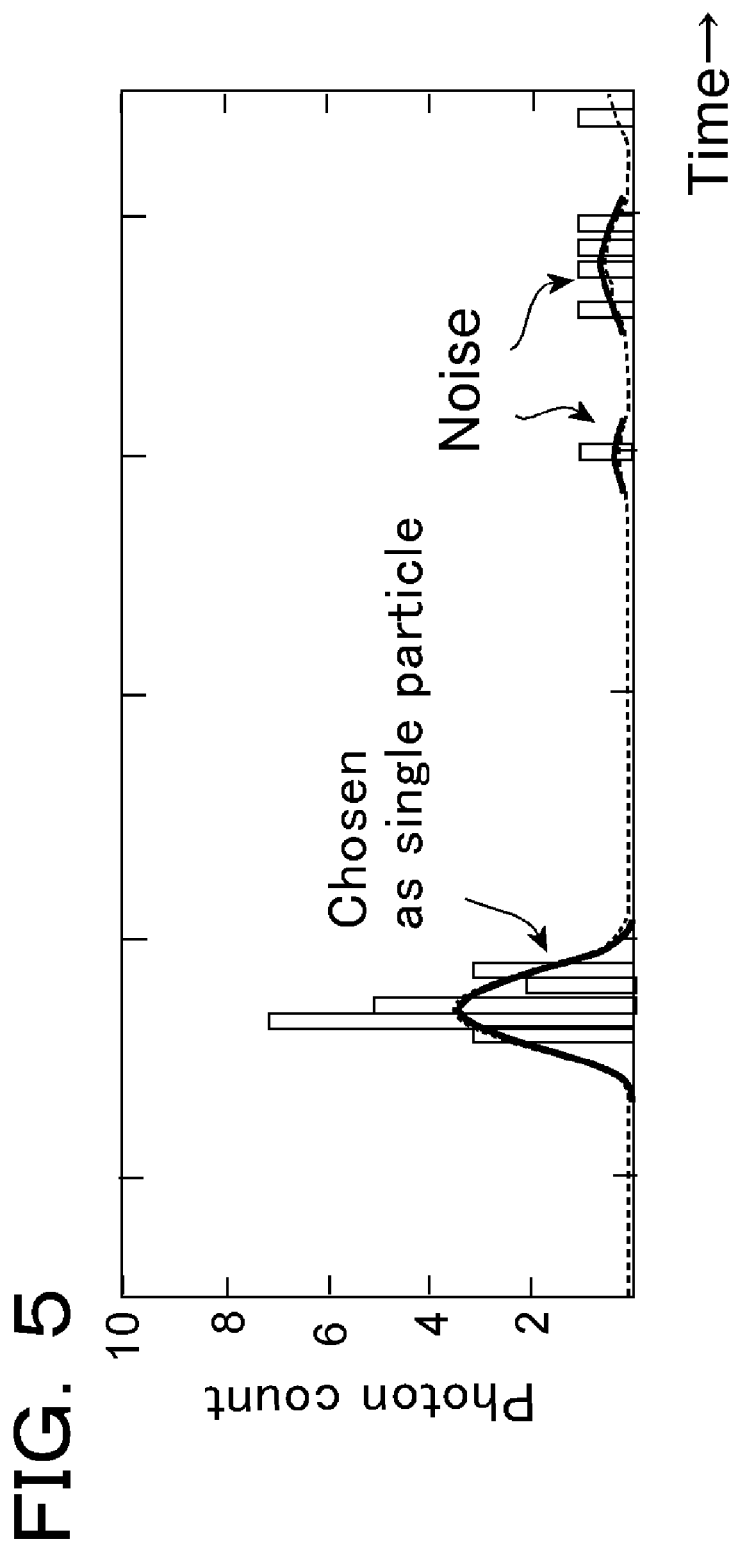

After that, a significant pulse signal is detected sequentially on the light intensity data (Steps 130-160). Concretely, first, on the time-differential value data of the light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed light intensity data in the pulse existing region (FIG. 4C, the lower row "bell-shaped function fitting"), and then, parameters of the pulse of the bell-shaped function, such as the peak intensity (the maximum). Ipeak; the pulse width (full width at half maximum), Wpeak; the correlation coefficient in the fitting (of the least square method), etc. are computed (step 140). In this regard, although the bell-shaped function to be used in the fitting is typically Gauss function as in Expression (8), it may be Lorentz type function. And, it is judged whether or not computed parameters of the bell shaped function are in the corresponding predetermined ranges assumed for the parameters of a bell shaped profile drawn by a pulse signal detected when one light-emitting particle passes through the light detection region, namely, whether or not the peak intensity, pulse width and correlation coefficient are in the corresponding predetermined ranges, respectively (step 150). Accordingly, as shown in FIG. 5 left, the signal, whose computed parameters of the bell-shaped function are judged to be within the ranges assumed in a signal corresponding to one light-emitting particle, is judged as a signal corresponding to one light-emitting particle, and thereby one light-emitting particle is detected. On the other hand, a pulse signal, whose computed parameters of the bell-shaped function are not within the assumed ranges, as shown in FIG. 5 right, is disregarded as noise. In this regard, simultaneously with detection of signal(s) of (a) light-emitting particle(s), the counting of the number of signals, i.e., the counting of light-emitting particles, may be performed.

The searching and the judgment of a pulse signal in the above-mentioned processes of steps 130-150 may be repetitively carried out in the whole regions of the light intensity data (step 160). In this regard, the process of detecting a signal of a light-emitting particle from light intensity data individually may be performed by an arbitrary way, other than the above-mentioned processes.

(ii) The Case of Performing the Digesting process after Detection of Signals of Light-Emitting Particles As shown in FIG. 3B, in a case that the digesting process (step 30) is performed after the detection process (step 20) of (a) signal(s) of (a) light-emitting particle(s), first, in the time series light intensity data obtained at step 10, the detection of a signal of a light-emitting particle is performed as it is according to the fitting of Expression (6) or the processes shown in FIG. 3C similarly to the above. In that case, the counting of the number of signals, i.e., the counting of light-emitting particles, may be performed simultaneously with the detection of (a) signal(s) of (a) light-emitting particle(s). Then, by choosing regions corresponding to the time sections of a predetermined width where a signal of a light-emitting particle exists in time series light intensity data and removing time sections where no signals of light-emitting particles exist as schematically drawn in FIG. 2D, the digested light intensity data is prepared.

(iii) Determination of Light-Emitting Particle Concentration

When the number of light-emitting particles has been determined by counting the number of signals of detected light-emitting particles, the number density or concentration of the light-emitting particle in the sample solution can be determined from the number of light-emitting particles and the volume of the whole region through which the light detection region has passed, if it is computed out by an arbitrary way (step 40).

The volume of the whole region through which the light detection region has passed may be theoretically computed out with the wavelength of excitation light or detected light, the numerical aperture of lenses and the adjustment condition of the optical system, but the volume may be determined experimentally, for instance, using the number of light-emitting particles detected by performing, with a solution having a known light-emitting particle concentration (a reference solution), the light intensity measurement, detection of (a) light-emitting particle(s) and their counting under the same condition as the measurement of a sample solution to be tested, and the light-emitting particle concentration of the reference solution. Concretely, for example, supposing the number of detected the light-emitting particles is N in a reference solution of the light-emitting particle concentration C, the whole volume Vt of the region through which Light detection region has passed is given by:

$$Vt = N/C \quad (6).$$

Alternatively, by preparing the plurality of solutions of different light-emitting particle concentrations and performing the measurement for each of the solutions, the average value of the computed Vt may be employed as the whole volume Vt of the region though which the light detection region has passed. Then, when Vt is given, the concentration c of the light-emitting particle of the sample solution, whose counting result of the light-emitting particles is n, is given by:

$$c = n/Vt \quad (7)$$

In this regard, the volume of the light detection region and the volume of the whole region which the light detection region has passed through may be given by an arbitrary method, for instance, using FCS and FIDA, instead of the above-mentioned method. Further, in the optical analysis device of this embodiment, there may be previously memorized in a storage device of the computer 18 the information on the relations (Expression (6)) between concentrations C and light-emitting particle numbers N of various standard light-emitting particles for assumed moving patterns of the light detection region, so that a user of the device can appropriately use the memorized information on the relation in conducting an optical analysis.

(iv) Storing, Indicating and Reading-In of Data

In the present invention, as described above, the digested light intensity data is prepared by removing regions where no signals of light-emitting particles exist from time series light intensity data, and thus, preferably, when data is stored in a storage device (not shown) of the computer 18, the digested light intensity data is stored. As shown in the following embodiments, since the size of digested light intensity data is substantially reduced, as compared with the size of time series light intensity data, by setting the above-mentioned time section of a predetermined with suitably, the storage area in the storage device can be saved significantly. Also, the digested light intensity data may be displayed on a display device of the computer 18. Further, the digested light intensity data stored in the storage device can be read-in, when various analyses and displaying of measurement results are performed certain time later after the performing of a light intensity measurement. In that case, the displaying and reading-in of data can be completed in a shorter time than the case of time series light intensity data.

Thus, according to the above-mentioned the present invention, in the scanning molecule counting method, the saving of storage area and the reduction of processing loads and time in various data processes will be achieved by preparing digested light intensity data by removing regions where no signals of light-emitting particles exist in time series light intensity data and using the digested light intensity data as data for the storing, displaying and analyses.

In order to verify the validity of the present invention explained above, the experiments described below were conducted. In this regard, it should be understood that the following embodiments illustrate the validity of the present invention only, not intended to limit the scope of the present invention.

Embodiment 1

In accordance with the way described above, digested light intensity data was prepared by removing regions where no signals of light-emitting particles existed from time series light intensity data obtained in a light measurement by the scanning molecule counting method, and the influence to the detection accuracy in performing detection of a signal of a light-emitting particle in the digested light intensity data and the size of the data volume reduced by the digesting were verified.

For a sample solution, there was prepared a solution containing fluorescent dye ATTO633 (Sigma-Aldrich, Cat. No. 18620) as a light-emitting particle at 10 pM in a phosphate buffer (including 0.05% Tween 20). In the light measurement, a single molecule fluorescence measuring apparatus MF20 (Olympus Corporation), equipped with the optical system of a confocal fluorescence microscope and a photon counting system, was used as the optical analysis device, and time series light intensity data (photon count data) was acquired for the above-mentioned sample solution in accordance with the manner explained in the above-mentioned "(2) Measurement of Light Intensity of a Sample Solution". In that time, a 633-nm laser light was used for excitation light, and, using a band pass filter, the light of the wavelength bands, 660 to 710 nm, was measured, and time series light intensity data was generated. The position of the light detection region in the sample solution was moved at the moving speed of 30 mm/second; BIN TIME was set to 10 μseconds and a measurement for 2 seconds was performed. After the light intensity measurement, in accordance with the procedures described in the above-mentioned "(3)(i) Detection of a Signal on Time Series Light Intensity Data.", the smoothing treatment was applied to the time series light intensity data acquired for the respective sample solutions, and after determining the start points and the end points of pulse signals in the smoothed data, the fitting of a Gauss function to each pulse signal was carried out by the least square method, and a peak intensity, a pulse width (full width at half maximum) and a correlation coefficient (in the Gauss function) were determined. In this case, the record count (the number of datum points) of time series light intensity data became 200,000 records ($2/10 \times 10^{-6}$), and data volume became about 1 MB.

Figure 6A:
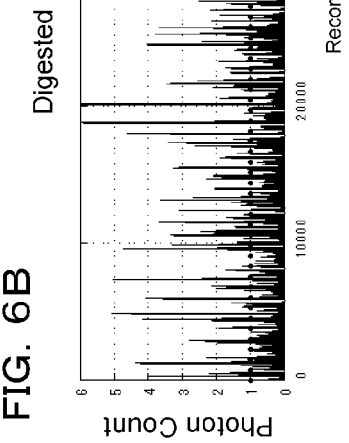
Figure 6A:
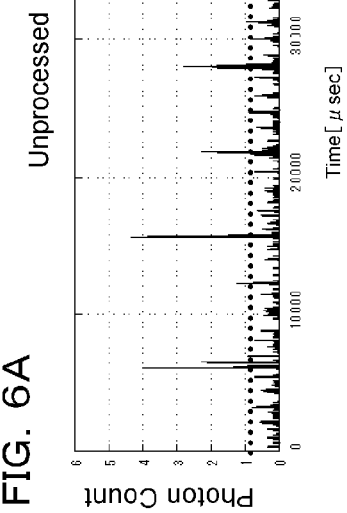

FIG. 6A shows a part of time series light intensity data in which the output obtained with the photodetector was made time series data. In this drawing, the upper row shows the photon count value in every 10 μseconds from the start of the measurement to 50000 μseconds, and the lower row shows the enlarged indication of the photon count values in every 10 μseconds from the start of the measurement to 5000 μseconds. With reference to this drawing, in the condition of the present experiment, it had been found that a signal of a light-emitting particle was a pulse form signal whose photon count value exceeded beyond 1 (the round dotted line in the drawing). Thus, as understood from the drawing of the upper row, in the time series light intensity data, the regions where a signal of a light-emitting particle actually appears are only part of the data, and the other regions are unnecessary regions. For instance, in the enlarged view shown in the lower row of FIG. 6A, the photon count values were less than 1 in the whole region, and thus, this region is unnecessary in the detection of a signal of a light-emitting particle.

Figure 6B:
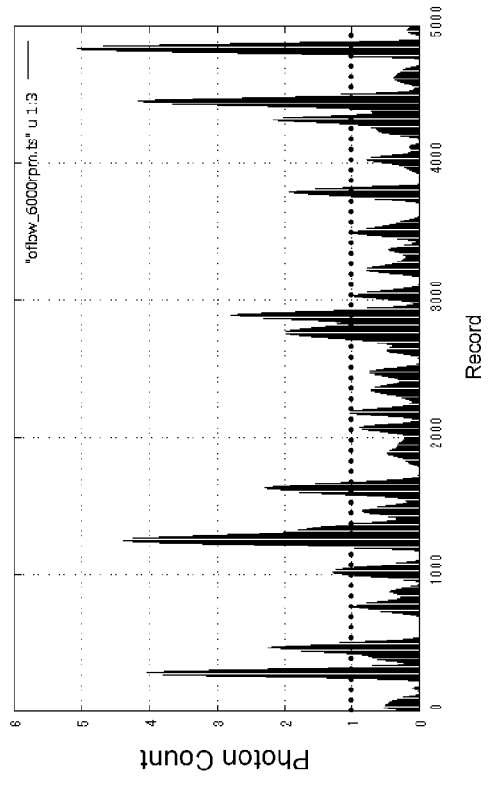
Figure 6B:
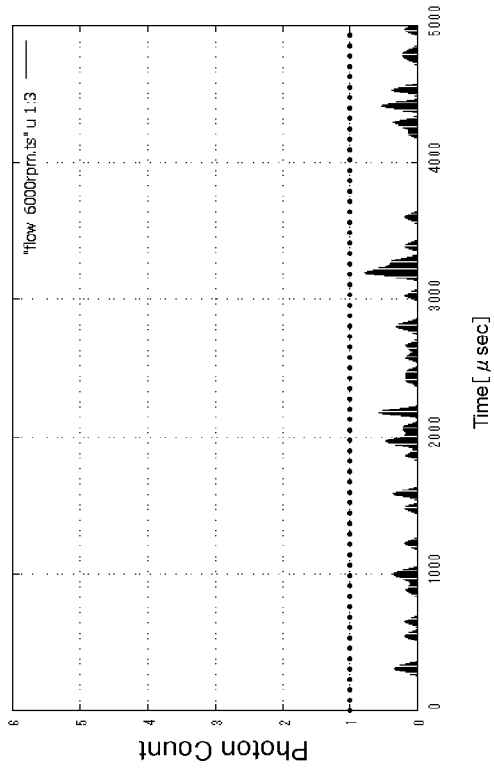

Thus, the digesting of time series light intensity data was performed in the way described in the above-mentioned digesting process [(i) The Case of Performing the Digesting process Before Detection of Signals of Light-emitting Particles]. Concretely, the time series light intensity data was divided into time sections of 200 μseconds and the total sum of photon counts was computed as the characteristic value of light intensity for every time section. Subsequently, regions corresponding to time sections whose total sum of photon counts exceeds beyond 5 (the threshold value for the characteristic value) were chosen, and thereby, the digested light intensity data in which regions corresponding to the other time sections had been deleted were prepared. The upper row of FIG. 6B shows the digested light intensity data obtained by carrying out the digesting of the time series light intensity data of FIG. 6A (from the start to the 5000th record), and the lower row of FIG. 6B shows the enlarged view of the upper row (from the start to the 500th records). As understood from the drawing in the digested light intensity data, the regions of less than 1 which is the threshold value for detection of a signal of a light-emitting particle have been reduced, and thereby unnecessary regions in the detection of a signal of a light-emitting particle were reduced.

When a signal of a light-emitting particle is detected using the digested light intensity data obtained by performing the digesting process as noted above, it is considered that the reduction of the accuracy of detection of a signal of a light-emitting particle, i.e., the increase of the number of undetectable signals of light-emitting particles would occur. Then, the influence of the predetermined width of a time section in dividing the time series light intensity data and the threshold value for a characteristic value in the digesting process on the accuracy of detection of a signal of a light-emitting particle was checked.

Concretely, in each of the cases of setting the predetermined width of the time section to 200 μseconds, 300 μseconds, 500 μseconds and 1000 μseconds in dividing the time series light intensity data, the individual detection of signals of light-emitting particles and counting of the number the signals were performed using each of the digested light intensity data obtained by performing a digesting process with setting the threshold value for characteristic value to 0-20. In the detection of signals of light-emitting particles, in accordance with the way described in "(b) Individual detection of a signal of a light-emitting particle" and FIG. 3C), a smoothing treatment was applied to the digested light intensity data, and after determining the start point and the end point of a pulse signal in the smoothed data, the fitting of the Gauss function was carried out to each pulse signal by the least-squares method, and thereby, the peak intensity, pulse width (full width at half maximum) and correlation coefficient (in the Gauss function) were determined. And, only the pulse signals satisfying the following conditions:

20 μsec.<pulse width<400 μsec.

Peak intensity>1 [pc/10 μsec.]

Correlation coefficient>0.95     (A)

were extracted as a signal of a light-emitting particle. Also, together with this, the ratios of the size of the digested light intensity data to the size of the time series light intensity data (data compression ratio) were checked.

The following table 1 shows the numbers (number of pulses) of detected signals of light-emitting particles and data compression ratios in each of the cases that the predetermined width (Window Size) of the time section in dividing the time series light intensity data was set to 200 μseconds-1000 μseconds and the threshold value (photon count threshold value) for the characteristic value was set to 5-20. In this connection, at photon count threshold value=0, the removing of regions was not conducted.

TABLE 1

| Window Size | Photon count threshold value | Number of pulses | Data compression ratio |
| --- | --- | --- | --- |
| 1000 μs | 0 | 761 | 100.0% |
|  | 5 | 759 | 80.0% |
|  | 10 | 749 | 48.7% |
|  | 15 | 669 | 32.6% |
|  | 20 | 535 | 22.0% |
| 500 μs | 0 | 761 | 100.0% |
|  | 5 | 759 | 40.1% |
|  | 10 | 663 | 19.3% |
|  | 15 | 507 | 12.1% |
|  | 20 | 352 | 7.9% |
| 300 μs | 0 | 761 | 100.0% |
|  | 5 | 754 | 20.7% |
|  | 10 | 596 | 9.9% |
|  | 15 | 416 | 6.1% |
|  | 20 | 276 | 3.9% |
| 200 μs | 0 | 761 | 100.0% |
|  | 5 | 734 | 12.3% |
|  | 10 | 540 | 6.0% |
|  | 15 | 348 | 3.6% |
|  | 20 | 220 | 2.2% |

With reference to the above-mentioned table, it has been shown that the data compression ratio becomes smaller, namely, the data volume will be reduced more in the smaller predetermined width, and in the case of the present experimental example, 200 μseconds was the optimum for the predetermined width (In the condition of this experimental example, the time of a light-emitting particle passing through the light detection region was about 74 μseconds, and thus, in the predetermined width of less than 200 μseconds, the possibility that the signal of one light-emitting particle appears over different time sections becomes higher, which is not preferable.). Moreover, in any predetermined width, when the threshold value for the characteristic value (photon count threshold value) was increased, the number of detected signals of the light-emitting particles decreased. This indicates that, when a threshold value for a characteristic value is set to an appropriate value, the reduction amount of the number of detected signals of light-emitting particles can be suppressed in an allowable degree.

Figure 7:
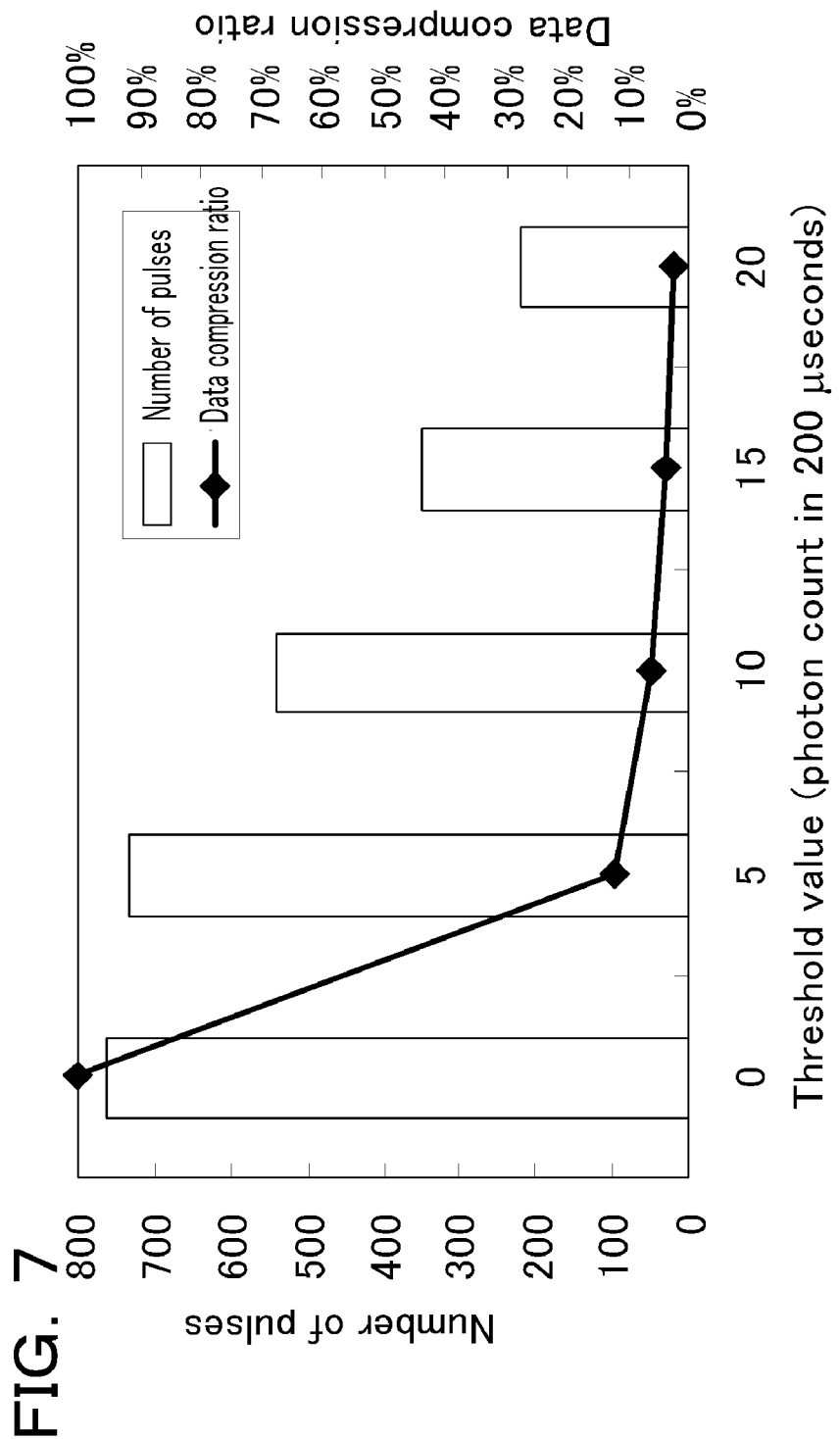
FIG. 7 is a graph chart showing the changes of the number of detected pulses and the data compression rate against threshold values for a characteristic value (the sum of photon counts) when the detection processing of a signal of a light-emitting particle is performed in the light intensity data obtained by carrying out the digesting process of the time series light intensity data.

FIG. 7 shows, in the form of a graph form, the detected number (number of pulses) of signals of light-emitting particles and the data compression ratio against the threshold values for the characteristic value in the case that the predetermined width was sets to 200 μseconds in the above mentioned table 1, respectively. With reference to the drawing, when the threshold value was set to 5, the data compression ratio became small to about 12% while the reduction amount of the detected number of signals of light-emitting particles was rarely observed. On other hand, when the threshold value was set to ten or more, the data volume was almost saturated with a slight reducing tendency, while the detected number of signals of light-emitting particles was reduced significantly. This suggests that a part of regions where (a) light-emitting particle(s) exists has been removed in the digesting process. Thus, in the case of the condition of the present experimental result, the digesting process can be performed in the optimum condition by dividing the time series light intensity data into time sections with setting then predetermined width to 200 μseconds and setting the threshold value for the characteristic value to 5. Moreover, it has been shown that, in accordance with the digesting process, it is possible to reduce data volume with suppressing the reduction of the accuracy in detection of a signal of a light-emitting particle as small as possible.

Embodiment 2

After performing individual detection of signals of light-emitting particles in time series light intensity data obtained in the light measurement by the scanning molecule counting method, the digesting process was performed to prepare digested light intensity data. For the time series light intensity data, the same data as Embodiment 1 was used, and the individual detection of signals of light-emitting particles was performed in the same manner as Embodiment 1. After that, the time series light intensity data were divided into time sections of a predetermined width, and regions where no signals of light-emitting particles exist were removed. In this regard, in the present embodiment, since the signals of light-emitting particles were detected in the time series light intensity data, no reduction of the accuracy of detection of signals of light-emitting particles occurred.

Figure 8:
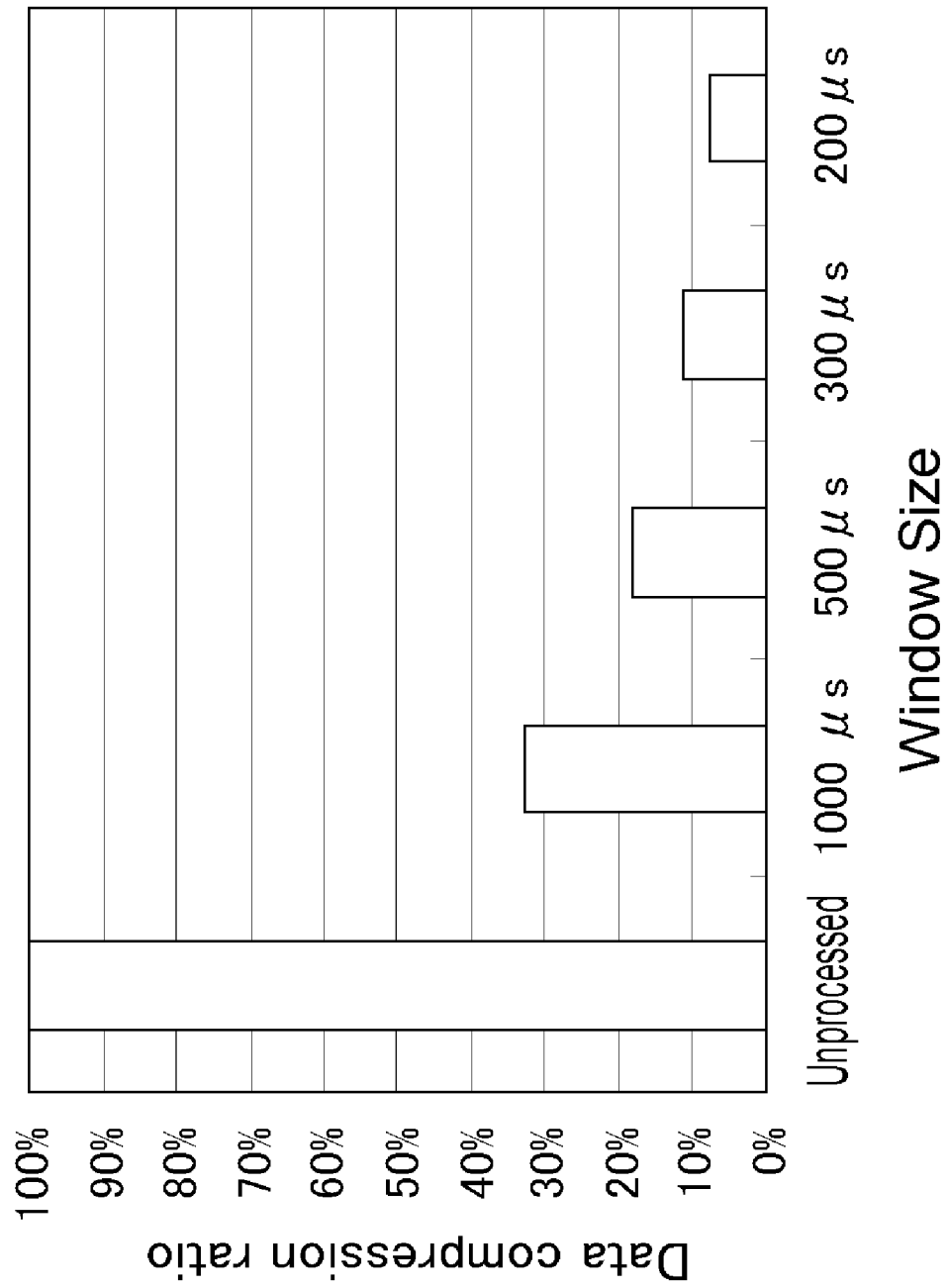
FIG. 8 is a graph chart showing a change, against window sizes, of the data compression rate of the light intensity data obtained by carrying out a digesting process after having performed the detection processing signals of light-emitting particles in the time series light intensity data.

FIG. 8 shows change of the data compression ratio when the predetermined width (window size) of the time section was changed. With reference to the drawing, the data volume became smaller as the predetermined width became smaller, and in the case of 200 μseconds of the predetermined width, the data compression ratio became 7.8%.

Thus, as understood from the results of the above-mentioned embodiments, by removing regions where no signals of light-emitting particles exist from time series light intensity data acquired in the scanning molecule counting method according to the teachings of the present invention, the reduction of data volume can be achieved with suppressing the reduction of the accuracy of detection of a signal of a light-emitting particle. Thereby, the saving of the memory volume of a storage device and the reduction of load and processing time in the data processing are achieved, and the expansion of the use range of the scanning molecule counting method is expected.

The invention claimed is:

1. An optical analysis device which detects light from a light-emitting particle dispersed and moving at random in a sample solution using an optical system of a confocal microscope or a multiphoton microscope, comprising:
   a light detection region mover for moving a position of a light detection region to another position of the light detection region in the optical system in the sample solution;
   a light detector which detects light from the light detection region; and
   a signal processor which generates time series light intensity data of the light from the light detection region detected with the light detector with moving the position of the light detection region in the sample solution and detects a signal indicating light from each light-emitting particle individually in the time series light intensity data;
   wherein the signal processor removes regions where no signal indicating light from each light-emitting particle exists in the time series light intensity data from the time series light intensity data, and
   wherein the signal processor smooths data values corresponding to light intensity variation over a plurality of units of time of a light signal from the particle.

2. The device of claim 1, wherein the signal processor computes out a characteristic value of light intensity which shows an presence or absence of light from a light-emitting particle in every time section of a predetermined width in the time series light intensity data; determines time sections where no signal indicating light from each light-emitting particle exists using the characteristic value; and removes regions corresponding to the time sections where no signal indicating light from each light-emitting particle exists from the time series light intensity data.

3. The device of claim 2, wherein the light detector detects the light from the light detection region by photon counting, and the time series light intensity data is time series photon count data.

4. The device of claim 3, wherein the characteristic value of light intensity is a value selected from a group of a total sum of photon counts, a center value of photon counts, an average of photon counts, an standard deviation of photon counts, a variance of photon counts, an entropy of photon counts, a maximum of photon counts and a particle count computed from a value of an autocorrelation function of photon counts when a correlation time is set to 0 in the time section of the predetermined width.

5. The device of claim 1, wherein the signal processor detects individually the signal indicating light from each light-emitting particle on light intensity data obtained by removing the regions where no signal indicating light from each light-emitting particle exists in the time series light intensity data from the light intensity data.

6. The device of claim 1, wherein the signal processor stores light intensity data obtained by removing the regions where no signal indicating light from each light-emitting particle exists in the time series light intensity data from the light intensity data, the light intensity data being stored in a storage device.

7. The device of claim 1, wherein the signal processor detects that one light-emitting particle has entered into the light detection region when a signal indicating light having a larger intensity than a predetermined threshold value has been detected.

8. The device of claim 1, wherein the light detection region mover moves the position of the light detection region at a velocity quicker than a diffusion moving velocity of the light-emitting particle.

9. The device of claim 1, wherein the light detection region mover moves the position of the light detection region by changing the optical path of the optical system.

10. The device of claim 1, wherein the signal processor determines a number density or concentration of the light-emitting particle in the sample solution based on the number of the detected light-emitting particles.

11. The device of claim 1, wherein the light detector detects the light from the light detection region by photon counting, and the time series light intensity data is time series photon count data.

12. An optical analysis method of detecting light from a light-emitting particle dispersed and moving at random in a sample solution using an optical system of a confocal microscope or a multiphoton microscope, comprising:
 (a) moving a position of a light detection region of the optical system in the sample solution;
 (b) detecting light from the light detection region during moving the position of the light detection region in the sample solution and generating time series light intensity data; and
 (c) detecting a signal indicating light from each light-emitting particle individually on the time series light intensity data;
 wherein the method comprises (d) removing regions where no signal indicating light from each light-emitting particle exists in the time series light intensity data from the time series light intensity data, and
 wherein the method further comprises smoothing data values corresponding to light intensity variation over a plurality of units of time of a light signal from the particle.

13. The method of claim 12, wherein, in the step (d), a characteristic value of light intensity which shows an presence or absence of light from a light-emitting particle in every time section of a predetermined width in the time series light intensity data is computed; time sections where no signal indicating light from each light-emitting particle exists using the characteristic value are determined; and regions corresponding to the time sections where no signal indicating light from each light-emitting particle exists are removed from the time series light intensity data.

14. The method of claim 13, wherein, in the step (b), the light from the light detection region is detected by photon counting, and the time series light intensity data is time series photon count data.

15. The method of claim 14, wherein the characteristic value of light intensity is a value selected from a group of a total sum of photon counts, a center value of photon counts, an average of photon counts, an standard deviation of photon counts, a variance of photon counts, an entropy of photon counts, a maximum of photon counts and a particle count computed from a value of an autocorrelation function of photon counts when a correlation time is set to 0 in the time section of the predetermined width.

16. The method of claim 12, wherein, in the step (c), the signal indicating light from each light-emitting particle is detected individually on light intensity data obtained by removing the regions where no signal indicating light from each light-emitting particle exists in the time series light intensity data from the light intensity data.

17. The method of claim 12, further comprising (e) storing light intensity data obtained by removing the regions where no signal indicating light from each light-emitting particle exists in the time series light intensity data from the light intensity data, the light intensity data being stored in a storage device.

18. The method of claim 12, wherein, in the step (c), it is detected that one light-emitting particle has entered into the light detection region when a signal indicating light having a larger intensity than a predetermined threshold value has been detected.

19. The method of claim 12, wherein, in the step (a), the position of the light detection region is moved at a velocity quicker than a diffusion moving velocity of the light-emitting particle.

20. The method of claim 12, wherein, in the step (a), the position of the light detection region is moved by changing the optical path of the optical system.

21. The method of claim 12, further comprising (f) determining a number density or concentration of the light-emitting particle in the sample solution based on the number of the detected light-emitting particles.

22. The method of claim 12, wherein, in the step (b), the light from the light detection region is detected by photon counting, and the time series light intensity data is time series photon count data.

23. A non-transitory computer readable storage device having a computer program product including programmed instructions for optical analysis of detecting light from a light-emitting particle dispersed and moving at random in a sample solution using an optical system of a confocal microscope or a multiphoton microscope, said programmed instructions causing a computer to perform steps of:
 moving a position of a light detection region of the optical system in the sample solution;
 detecting light from the light detection region during moving the position of the light detection region in the sample solution generating time series light intensity data; and
 detecting a signal from each light-emitting particle individually in the time series light intensity data,
 wherein said programmed instructions further causes a computer to perform a step of removing regions where no signal indicating light from each light-emitting particle exists in the time series light intensity data from the time series light intensity data
 wherein said programmed instructions further causes the computer to smooth data values corresponding to light intensity variation over a plurality of units of time of a light signal from the particle.

24. The non-transitory computer readable storage device of claim 23, wherein, in the step of removing regions where no signal indicating light from each light-emitting particle exists in the time series light intensity data from the time series light intensity data, a characteristic value of light intensity which shows an presence or absence of light from a light-emitting particle in every time section of a predetermined width in the time series light intensity data is computed; time sections where no signal indicating light from each light-emitting particle exists using the characteristic value are determined; and regions corresponding to the time sections where no signal indicating light from each light-emitting particle exists are removed from the time series light intensity data.

25. The non-transitory computer readable storage device of claim 24, wherein, in the step of detecting light from the light detection region and generating time series light intensity data, the light from the light detection region is detected by photon counting, and the time series light intensity data is time series photon count data.

26. The non-transitory computer readable storage device of claim 25, wherein the characteristic value of light intensity is a value selected from a group of a total sum of photon counts, a center value of photon counts, an average of photon counts, an standard deviation of photon counts, a variance of photon counts, an entropy of photon counts, a maximum of photon counts and a particle count computed from a value of an autocorrelation function of photon counts when a correlation time is set to 0 in the time section of the predetermined width.

27. The non-transitory computer readable storage device of claim 23, wherein, in the step of detecting a signal indicating light from each light-emitting particle individually on the time series light intensity data, the signal indicating light from each light-emitting particle is detected individually on light intensity data obtained by removing the regions where no signal indicating light from each light-emitting particle exists in the time series light intensity data from the light intensity data.

28. The non-transitory computer readable storage device of claim 23, wherein said programmed instructions further causes a computer to perform a step of storing light intensity data obtained by removing the regions where no signal indicating light from each light-emitting particle exists in the time series light intensity data from the light intensity data, the light intensity data being stored in a storage device.

29. The non-transitory computer readable storage device of claim 23, wherein, in the step of detecting a signal indicating light from each light-emitting particle individually, it is detected that one light-emitting particle has entered into the light detection region when a signal indicating light having a larger intensity than a predetermined threshold value has been detected.

30. The non-transitory computer readable storage device of claim 23, wherein, in the step of moving the position of the light detection region, the position of the light detection region is moved at a velocity quicker than a diffusion moving velocity of the light-emitting particle.

31. The non-transitory computer readable storage device of claim 23, wherein, in the step of moving the position of the light detection region, the position of the light detection region is moved by changing the optical path of the optical system.

32. The non-transitory computer readable storage device of claim 23, wherein said programmed instructions further causes a computer to perform a step of determining a number density or concentration of the light-emitting particle in the sample solution based on the number of the detected light-emitting particles.

33. The non-transitory computer readable storage device of claim 23, wherein, in the step of detecting light from the light detection region and generating time series light intensity data, the light from the light detection region is detected by photon counting, and the time series light intensity data is time series photon count data.

* * * * *